(12) United States Patent
Bai et al.

(10) Patent No.: US 7,522,744 B2
(45) Date of Patent: Apr. 21, 2009

(54) SYSTEM AND METHOD FOR ADAPTIVE BOLUS CHASING COMPUTED TOMOGRAPHY (CT) ANGIOGRAPHY

(75) Inventors: Er-wei Bai, Iowa City, IA (US); Ge Wang, Iowa City, IA (US); Michael W. Vannier, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 709 days.

(21) Appl. No.: 11/215,733

(22) Filed: Aug. 29, 2005

(65) Prior Publication Data

US 2006/0178836 A1 Aug. 10, 2006

Related U.S. Application Data

(60) Provisional application No. 60/605,865, filed on Aug. 31, 2004.

(51) Int. Cl.
*G06K 9/00* (2006.01)
*G06F 19/00* (2006.01)
*A61B 6/00* (2006.01)

(52) U.S. Cl. .............................. 382/100; 702/19; 378/4

(58) Field of Classification Search ................ 382/100, 382/128–134; 600/407, 410, 411, 415–420, 600/425, 431, 436; 378/4, 8, 20–28, 901; 702/19, 150, 182, 183; 128/920; 424/9.4
See application file for complete search history.

(56) References Cited

U.S. PATENT DOCUMENTS

| | | | |
|---|---|---|---|
| 5,713,358 A | 2/1998 | Mistretta | |
| 5,830,143 A | 11/1998 | Mistretta | |
| 5,839,440 A | 11/1998 | Liou et al. | |
| 5,960,054 A * | 9/1999 | Freeman et al. | ................ 378/4 |
| 6,075,836 A | 6/2000 | Ning | |
| 6,230,040 B1 | 5/2001 | Wang et al. | |
| 6,351,513 B1 | 2/2002 | Bani-Hashemi et al. | |
| 6,389,104 B1 | 5/2002 | Bani-Hashemi et al. | |
| 6,397,098 B1 | 5/2002 | Uber et al. | |
| 6,535,821 B2 | 3/2003 | Wang et al. | |
| 6,577,887 B2 * | 6/2003 | Wolff et al. | .................. 600/420 |
| 6,597,938 B2 * | 7/2003 | Liu | ............................ 600/420 |

(Continued)

OTHER PUBLICATIONS

Tam, K. C., S. Samarasekera, et al. (1998). "Exact cone beam CT with a spiral scan." Phys. Med. Biol. 43(4):1015-1024.

(Continued)

*Primary Examiner*—Abolfazl Tabatabai
(74) *Attorney, Agent, or Firm*—Ballard Spahr Andrews & Ingersoll, LLP

(57) ABSTRACT

A method of utilizing bolus propagation and control for contrast enhancement comprises measuring with an imaging device a position of a bolus moving along a path in a biological structure. The method further comprises predicting a future position of the bolus using a simplified target model and comparing the predicted future position of the bolus with the measured position of the bolus. A control action is determined to eliminate a discrepancy, if any, between the predicted position of the bolus and the measured position of the bolus and the relative position of the imaging device and the biological structure is adaptively adjusted according to the control action to chase the motion of the bolus.

68 Claims, 10 Drawing Sheets

U.S. PATENT DOCUMENTS

| | | |
|---|---|---|
| 6,614,878 B2 | 9/2003 | Bogatu et al. |
| 2002/0010551 A1 | 1/2002 | Wang et al. |
| 2003/0036694 A1 | 2/2003 | Liu |

OTHER PUBLICATIONS

Tublin ME, Tessler FN, Cheng SL, Peters TL, McGovern PC, "Effect of injection rate of contrast medium on pancreatic and hepatic helical CT," 1999, Radiology, 210:97-101.

Wang G et al, "A model on intravenous bolus propogation for optimization of contrast enhancement," 2000, Proc. SPIE, 3978:436-447.

Wang G, Brink JA, Vannier MW: Theoretical FWTM values in helical CT. Med Phys 1994,21(6):753-754.

Wang G, Crawford CE, Kalender WA, "Multirow detector and cone-beam spiral/helical CT," 2000, IEEE Trans. Med. Imaging, 19(9):817-821.

Wang G, Frei T, Vannier MW: Fast algorithm for metal artifact reduction in X-ray CT. Academic Radiology 7(8):607-614, 2000.

Wang G, Li Y: Axiomatic approach for quantification of image resolution. IEEE Signal Processing Letters 6(10):257-258, 1999.

Wang G, Lin TH, Cheng PC, Shinozaki DM: A general cone-beam reconstruction algorithm. IEEE Trans. Med. Imaging 12(3):486-496, 1993.

Wang G, Schweiger GD, Vannier MW, "An iterative algorithm for X-ray CT fluoroscopy," 1998, IEEE Trans Med Imag, 17(5):853-856.

Wang G, Snyder DL, O'Sullivan Jam Vannier MW: Iterative deblurring for metal artifact reduction. IEEE Trans. on Medical Imaging 15(5):657-664, 1996.

Wang G, Vannier MW, Skinner MW, Cavalcanti MGP, Harding G: Spiral CT image deblurring for cochlear implantation. IEEE Transactions on Medical Imaging 17(2):251-262, 1998.

Wang G, Vannier MW: Helical CT image noise—Analytical results. Med. Phys. 1993;20(6):1635-1640.

Wang G, Vannier MW: Longitudinal resolution in volumetric X-ray CT-Analytical comparison between conventional and helical CT. Medical Physics 21(3):429-433, 1994.

Wang G, Vannier MW: Low-contrast resolution in volumetric X-ray CT-Analytical comparison between conventional and spiral CT. Medical Physics 24(3):373-376, 1997.

Wang G, Vannier MW: Optimal pitch in spiral computed tomography. Medical Physics 24(10):1635-1639, 1997.

Wang G, Vannier MW: Spatial variation of section sensitivity profile in helical CT. Med Phys, 1994, 21(9):1491-1497.

Wang G, Vannier MW: Stair-step artifacts in three-dimensional helical CT—An experimental study. Radiology 191(1):79-83, 1994.

Wang G, Vannier MW: The effect of pitch in multi-slice spiral/helical CT. Med. Phys. 26(12): 2648-2653, 1999.

Wang G, Zhao SY, Heuscher D: A knowledge-based cone-beam X-ray CT algorithm for dynamic volumetric cardiac imaging. Med. Phys. 29(8):1807-1822, 2002.

Wang G: X-ray micro-CT with a displaced detector array. Med. Phys. 29(7):1634-1636, 2002.

Wang Y et al, "Timing algorithm for bolus chase MR digital subtraction angiography," 1998, Magnetic Resonance in Medicine, 39(5):691-696.

Wang Y et al., "Bolus-chase MR digital subtraction angiography of the entire the lower extremity in one minute," 1998, Radiology, 207:263-269.

Wang, G. and M. W. Vannier (1995). "Preliminary syudy on helical CT algorithms for patient motion estimation and compensation." IEEE Trans. Medical Imaging 14(2): 205-211.

Watanabe N, "Development of a half-second real-time helical CT scanner, AquillonTM," Medical Review, 68:39-43.

Watts R et al, "Anatomically tailored k-space sampling for bolus chase 3D MR digital subtraction angiography," 2001, Radiology, 218:899-904.

Wu Z et al, "Real-Time Tracking of Contrast Bolus Propagation in X-Ray Peripheral Angiography," 1998, IEEE Workshop on Biomedical Image Analysis, 164-172.

Zhao SY, Wang G: Feldkamp-type cone-beam tomography in the wavelet framework. IEEE Trans. Med. Imaging 19(9):922-929, 2000.

Bae KT, Heiken JP, Brink JA, "Aortic and hepatic contrast medium enhancement at CT: Part I. Prediciton with a computer model," 1998 Radiology, 207:647-655.

Bae KT, Heiken JP, Brink JA, "Aortic and hepatic contrast medium enhancement at CT: Part II. Effect of reduced cardiac output in a Porcine Model," 1998, Radiology, 207:657-662.

Bai EW, "A blind approach to the Hammerstein-Wiener model identification," 2002, Autimatica, 38(6):967-979.

Bai EW, "Frequency domain identification of Hammerstein models," 2003, IEEE Trans on Automatic Control, 48(4):530-542.

Bai EW, Huang Y, "Variable gain parameter estimation algorithms for fast tracking and smooth steady state," 2000, Automatica, 36(7):1001-1008.

Bai EW, Wang G, Sharafuddin MJ, Bennett JR, Halloran JI, Vannier M, Bai, "Study of an Adaptive Bolus Chasing CT Angiography," (2006) Journal of X-Ray Science and Tech., 14(1):27-38.

Bassingthwaighte J, Ackerman FH, Wood, EH, "Application of the lagged normal density curve as a model for arterial dilution curves," 1966, Circulation Research, 18(4):398-415.

Bennett J, Bai EW, Halloran J, Wang G, "A preliminary study on adaptive field-of-view tracking in peripheral digital subtraction angiography," 2003, J of X-Ray Science and Technology, 11:149-159.

Berland LL, "Slip-ring and conventional dynamic hepatic CT: Contrast material and timing considerations," 1995, Radiology, 195(1):1-8.

Blomley et al,. "Bolus dynamics: Theoretical and experimental aspects," 1997, The British Journal of Radiology, 70(832):351-359.

Boos M et al, "Contrast-Enhanced Magnetic Resonance Angiography of Peripheral Vessels," 1998, Investigative Radiology, 33(9):538-546.

Browne J, De Pierro AR, "A row-action alternative to the EM algorithm for maximizing likelihoods in emission tomography," 1996, IEEE Trans Med Imag, 15(5):687-699.

Cademartiri F et al, "Parameters Affecting Bolus Geometry in CTA: A Review," 2002, J. of Computer Assisted Tomography, 26(4):598-607.

Claves JL, et al, "Evaluation of contrast densities in the diagnosis of carotid stenosis by CT angiography," 1997, AJR, 169(2):569-573.

Crawford, C. R. K. F. King (1990). "Computed tomography scanning with simultaneous patient translation." Med. Phys. 17(6): 967-982.

Defrise M., Noo F., Kudo H., "A solution to the long-object problem in helical cone-beam tomography", 2000, Phys. Med. Biol., vol. 45(3):623-644.

Fleischmann D and K. Hittmair, "Mathematical Analysis of Arterial Enhancement and Optimization of Bolus Geometry for CT Angiography Using the Discrete Fourier Transform," 1999, J Comput Assist Tomog, 23(3):474-484.

Foley et al., "Technical developments and instrumentation, digital subtraction angiography of the extremities using table translation," 1985, Radiology, 157:255-258.

Foo T et al, "Automated Detection of Bolus Arrival and Initiation of Data Acquisition in Fast, Three-dimensional, Gadolinium-enhanced MR Angiography," 1997b, Radiology, 203(1):275-280.

Gullberg, G. T. and G. L. Zeng (1992). "A cone-beam filtered backprojection reconstruction algorithm for cardiac single photon emission computed tomography." IEEE Trans. Medical Imaging 11(1):91-101.

Heiken JP, Brink JA, Vannier MW: Spiral (Helical) CT. Radiology 1993; 189(3):647-656.

Heussel CP, Viogtlaender T, Kauczor H, Braun M, Meyer J, Thelen M, "Detection of coronary artery calcifications predicting coronary heart disease: Comparison of fluoroscopy and spiral CT," 1998, Eur. Radiol., 8(6):1016-1024.

Ho V et al, "Optimization of Gadolinium-Enhanced Magnetic Resonance Angiography Using an Automated Bolus-Detection Algorithm (MR SmartPrep)," 1998, Investigative Radiology, 33(9):515-523.

Hsieh, J, "Analysis of the temporal response of computed tomography fluoroscopy," 1997, Med Phys, 24(5):665-675.

Hubener KH, Kalender WA, Metzger HF, "Fast digital recording of x-ray dilution curves: A preliminary evaluation," 1982, Radiology, 145(2):545-547.

Jiang M, Wang G, Skinner MW, Rubinstein JT, Vannier MW: Blind deblurring of spiral CT images-comparative studies on edge-to-noise ratios. Med Phys, 2002;29(5):821-829.

Jiang M, Wang G: Convergence studies on iterative algorithms for image reconstruction, 2003, IEEE Trans. Med. Imaging 22(5): 569-579.

Jurriaans et al., "Bolus Chasing: A new technique in peripheral arteriography," 1993, Clinical Radiology, 48(3):182-185.

Kachelriess, M., S. Ulzheimer, et al. (2000). "ECG-correlated image reconstruction from subsecond multi-splice spiral CT scans of the heart." Med. Phys. 27(8): 1881-1902.

Katada K, "Half-second, half-millimeter real-time multislice helical CT: CT diagnosis using AquillonTM," 1999, Medical Review, 68(1):31-38.

Katsevich A, "Improved exact FBP algorithm for spiral CT," 2004 Adv. Appl. Math. 32: 681-697.

Kopka L, Rodenwalt J, Fischer U, Mueller DW, Oestmann JW, Grabbe E, "Dual-phase helical CT of the liver: Effects of bolus tracking and different volumes of contrast material," 1996, Radiology, 201(2):321-326.

Kump K et al, "Comparison of Algorithms for Combining X-Ray Angiography Images," 2001, IEEE Trans. On Med. Imaging, 20(8):742-750.

Kuszyk BS, Beauchamp NJ, Fishman EK, "Neurovascular applications of CT angiography," 1998, Semin. Ultrasound. CT MR, 19:394-404.

Lee SW, Wang G, "A Grangeat-type half-scan algorithm for cone-beam CT", 2003, Med Phys., 30(4): 689-700.

Liu, Y., H. Liu, et al. (2001). "Half-scan cone-beam CT fluoroscopy with multiple x-ray sources." Med. Phys. 28(7): 1466-1471.

Luboldt, W., R. Weber, et al. (1999). "Influence of helical CT parameters on spatial resolution in CT angiography performed with a subsecond scanner," Investigative Radiology 34(6): 421-426.

Malden, E. S., D. Picus, et al. (1994). "Peripheral vascular disease: evaluation with stepping DSA and conventional screen-film angiography." Radiology 191(1): 149-153.

Meinel Jr. JF, Wang G, Jiang M, Frei T, Vannier MW, Hoffman EA: Spatial variation of resolution and noise in multi-detector row spiral CT. Academic Radiology, 2003, 10(6):607-613.

Napel S, Marks MP, Rubin GD, Jeffrey RB, Dake MD, Enzmann DR, et al., "CT angiography using spiral CT and maximum intensity projections," 1992, Radiology, 185:607-610.

Ohnesorge, B., T. Flohr, et al. (2000). "Cardiac imaging by means of electrocardiographically gated multisection spiral CT: initial experience." Radiology 217: 564-571.

Ohnesorge, B., T. Flohr, et al. (2000). "Efficient correction for CT image artifacts caused by objects extending outside the scan field of view." Med. Phys. 27(1): 39-46.

Prince M et al, "Contrast-enhanced Abdominal MR Angiography: Optimization of Imaging Delay Time by Automating the Detection of Contrast Material Arrival in the Aorta," 1997, Radiology, 203(1):109-114.

Raptopoulos V, Rosen MP, Kent KC, Kuestner LM, Sheiman RG, Pearlman JD, "Sequential helical CT angiography of aortoiliac disease," 1996, AJR 166(6):1347-1354.

Rieker O, Duber C, Neufang A, Pitton M, Schweden F, Thelen M, "CT angiography versus intraarterial digital subtraction angiography for assessment of aortoiliac occlusive disease, " 1997, AJR, 169:1133-1138.

Rubin GD et al, "Mulit-detector row CT angiography of lower extremity arterial inflow and runoff: initial experience," 2001, Radiology, 221(1):146-158.

Rubin GD, Paik DS, Johnston PC, Napel S, "Measurement of the aorta and its branches with helical CT," 1998, Radiology, 206(3):823-829.

Schwartz RB, Jones KM, Chernoff DM, Mukherji SK, Khorasani R, Tice HM, et al., "Common carotid artery bifurcation: Evaluation with spiral CT. Work in progress," 1992, Radiology, 185(2):513-519.

Schweiger GD, Chang PC, Brown BP, "Optimizing contrast enhancement during helical CT of the liver: A comparison of two bolus tracking techniques," 1998, AJR, 171:1551-1558.

Sheafor DH, Keogan MT, DeLong DM, Nelson RC, "Dynamic helical CT of the abdomen: Prospective comparison of pre- and postprandial contrast enhancement," 1998, Radiology, 206:359-363.

Silverman PM, Roberts SC, Ducic I, Tefft MC, Olson MC, Cooper C, Zeman RK, "Assessment of a technology that permits individualized scan delays on helical hepatic CT: A technique to improve efficiency in use of contrast material," 1996, AJR 167:79-84.

Snyder D., Schulz T. O'Sullivan J., "Deblurring Subject to Non-negativity Constraints," IEEE Trans. on Signal Processing, vol. 40, pp. 1143-1150, May 1992.

Stehling MK, JA Lawrence et al, "CT angiography: expanded clinical applications," 1994, American Journal of Roentgenol, 163(4):947-955.

Taguchi, K. and H. Aradate (1998). "Algorithm for image reconstruction in multi-slice helical CT." Med. Phys. 25(4): 550-561.

Takase K, "Helical CT with SureStart for the examination of patients with vascular disease," Medical Review, 67:17-21.

* cited by examiner

SYSTEM AND METHOD FOR ADAPTIVE BOLUS CHASING COMPUTED TOMOGRAPHY (CT) ANGIOGRAPHY

CROSS REFERENCE TO RELATED APPLICATIONS

This application claims the benefit of U.S. Provisional Application No. 60/605,865, filed Aug. 31, 2004. The aforementioned application is herein incorporated in its entirety by reference.

ACKNOWLEDGMENT

This invention was made partially with government support under NIH/NIBIB grants EB001685 and EB002667-01 awarded by the National Institutes of Health. The government has certain rights in the invention.

BACKGROUND OF THE INVENTION

1. Field of Invention

The present invention generally relates to bolus-chasing angiography wherein imaging data is analyzed more effectively, tolerating greater modeling errors and uncertainties, using more powerful and robust control techniques and incorporating faster and more robust identification/estimation algorithms and techniques.

2. Description of Prior Art

As known in the prior art, administration of a contrast material or bolus provides a short temporal window for optimally imaging the vasculature, lesions and tumors. Optimization of contrast enhancement becomes increasingly crucial with the wide use of CT and Magnetic Resonant Image ("MRI") technology, given the dramatically shortened image acquisition time. Recently, CT began a transition into subsecond scanning, cone-beam geometry and real-time imaging with the introduction of multi-slice/cone-beam systems.

A number of clinical studies were reported on contrast enhancement for CT in the past. However, the existing results on modeling of CT contrast bolus dynamics are very limited.

To obtain the highest image quality in CT angiography at the lowest dosage of contrast material, strategies for bolus administration and CT data acquisition must be individualized and optimized. It is desirable to scan when the intravascular concentration of contrast material is at its peak.

Scanning too early may result in over-estimation of stenosis, while scanning too late may result in overlap of venous structures.

Three methods have been developed to individualize scan timing:

(1) test-bolus timing,
(2) region of interest (ROI) threshold triggering, and
(3) visual cue triggering.

For the test-bolus method, there is a risk of decreasing target lesion conspicuity due to equilibration of the test-bolus. For the two triggering methods, they are vulnerable to patient motion, usually related to breathing, which may displace the target organ or vessel from the scan plane.

Moreover, one of the fundamental limitations with all the three methods is that they provide little data for matching the table/gantry translation to the contrast bolus propagation. Bolus dynamics is complicated by multiple interacting factors involving the contrast administration protocol, imaging techniques, and patient characteristics. In particular, the current patient table is translated at a pre-specified constant speed during data acquisition, which cannot be altered adaptively to chase the contrast bolus for optimally enhanced CT images.

With a pre-set scanning speed, it is difficult and often impossible to synchronize the central scanning plane with the longitudinal bolus position. This misalignment becomes more problematic to image quality when spiral scanning speed is fast (with multi-slice spiral CT), contrast volume is small and/or injection rate is high (leading to reduced peak duration), as well as when there are large or small capacity vessels, either from aneurysm formation or occlusive disease.

U.S. Pat. No. 6,535,821 (Wang et al.) (the '821 patent), which is incorporated herein in its entirety by reference thereto, discloses a system and method for optimization of contrast enhancement utilizing a bolus propagation model, a computerized predictor of the bolus position, and a real-time tomographic imaging system with an adaptive mechanism to move a patient and/or the imaging components (either the entire gantry or its essential parts).

In the '821 patent, a monitoring means for measuring the position of a bolus moving along a path in a biological structure is provided. A predicted position of the bolus is determined using a bolus propagation model with a set of parameters. The predicted position of the bolus is compared with the measured position of the bolus. A filtering means is provided for reconciling a discrepancy, if any, between the predicted position of the bolus and the measured position of the bolus, to derive a set of control parameters. Finally, a control means is provided for receiving the set of control parameters, to adaptively transport the table to chase the moving bolus.

While the system and method disclosed in the '821 patent represents a major improvement over prior systems and methods, there is a need for making the implementation of bolus chasing imaging in practice efficient and possible by reconstructing and analyzing imaging data in more effective ways, tolerating greater modeling errors and uncertainties, using more powerful and robust control techniques, and incorporating faster and more robust identification/estimation algorithms and techniques.

SUMMARY OF THE INVENTION

A method of utilizing bolus propagation and control for contrast enhancement comprises measuring with an imaging device a position of a bolus moving along a path in a biological structure. The method further comprises predicting a future position of the bolus using a simplified target model and comparing the predicted future position of the bolus with the measured position of the bolus. A control action is determined to eliminate a discrepancy, if any, between the predicted position of the bolus and the measured position of the bolus and the relative position of the imaging device and the biological structure is adaptively adjusted according to the control action to chase the motion of the bolus.

A system for utilizing bolus propagation and control for contrast enhancement comprises an imaging device for measuring a position of a bolus moving along a path in a biological structure. The system further comprises a predictor comprising a processor programmed for predicting a future position of the bolus using a simplified target model and a processor programmed for comparing the predicted future position of the bolus with the measured position of the bolus. A controller comprising a processor is programmed for determining a control action to eliminate a discrepancy, if any, between the predicted position of the bolus and the measured position of the bolus. The system further comprises an actuator for adaptively adjusting the relative position of the imaging device and the biological structure according to the control action to chase the motion of the bolus.

Additional advantages of the invention will be set forth in part in the description which follows, and in part will be obvious from the description, or may be learned by practice of the invention. The advantages of the invention will be realized and attained by means of the elements and combinations particularly pointed out in the specification. It is to be understood that both the foregoing general description and the following detailed description are exemplary and explanatory only and are not restrictive of the invention, as claimed.

BREIF DESCRIPTION OF THE DRAWINGS

The accompanying drawings, which are incorporated in and constitute a part of this specification, illustrate one embodiment of the invention and together with the description, serve to explain the principles of the invention.

Figure 5:
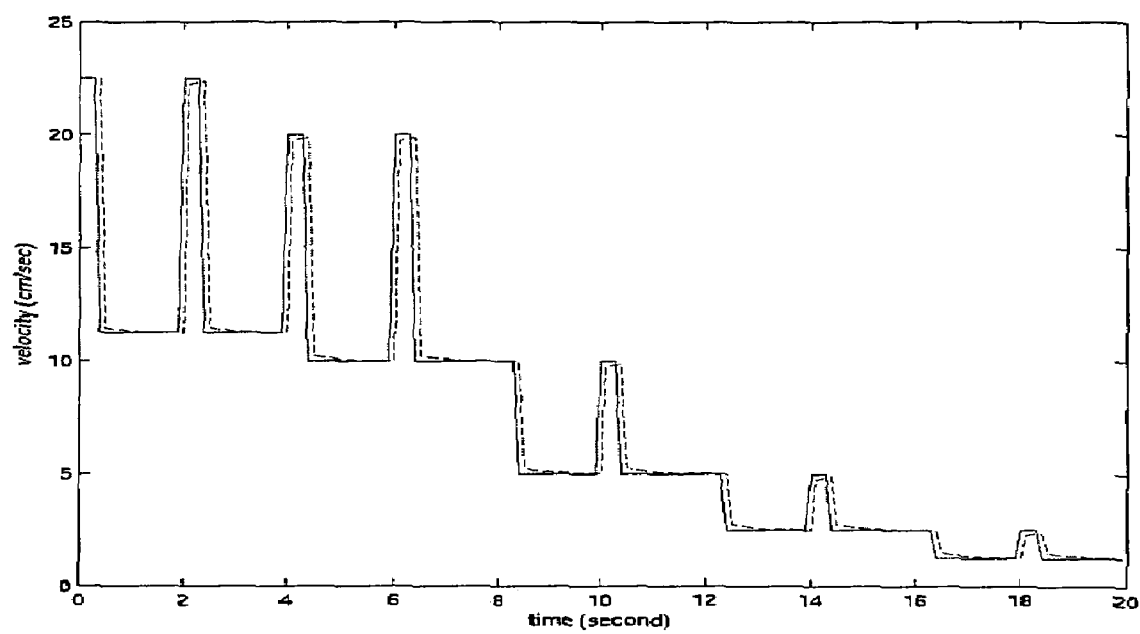

FIG. 5 shows computer simulation data of bolus-chasing CT angiography, where the actual bolus velocity in the various positions in the vascular tree is represented by the solid line and the controlled table velocity based on the adaptive control technique is represented by the dashed line. The actual velocity curve is modeled as a stepping function according to vascular tree level under physiologic conditions, taking into account changes between systolic and diastolic phases.

Figure 6:
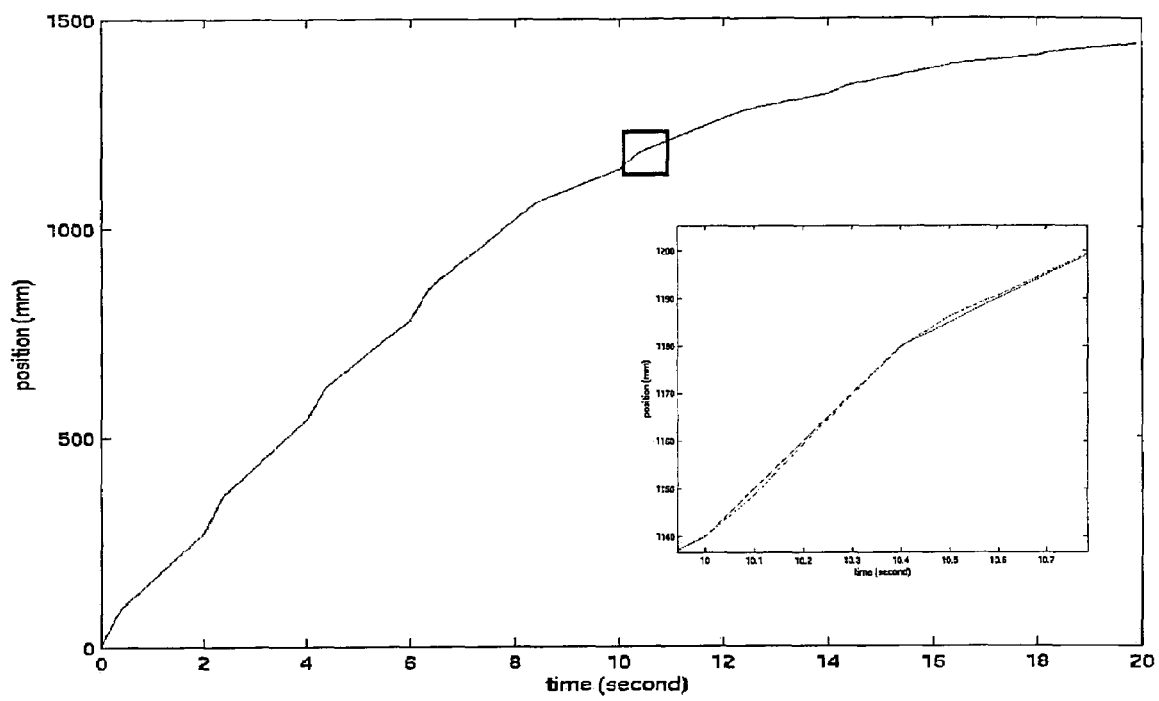

FIG. 6 shows plots of the simulated actual bolus position (solid line) and the controlled/predicted patient table position (dashed line). The maximum error is less than 1 mm.

Figure 7:
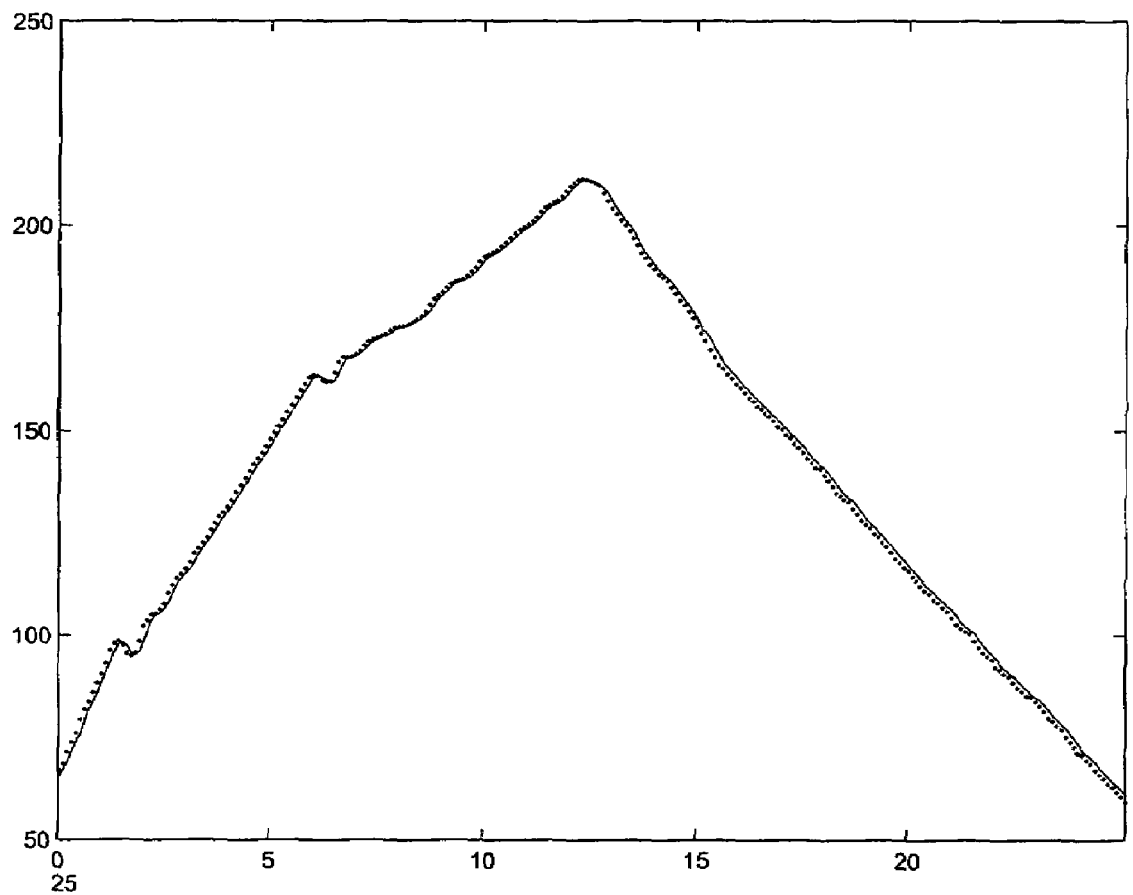

FIG. 7 shows the simulated actual bolus position (solid line) and the controlled table position (dash-dotted line).

Figure 8:
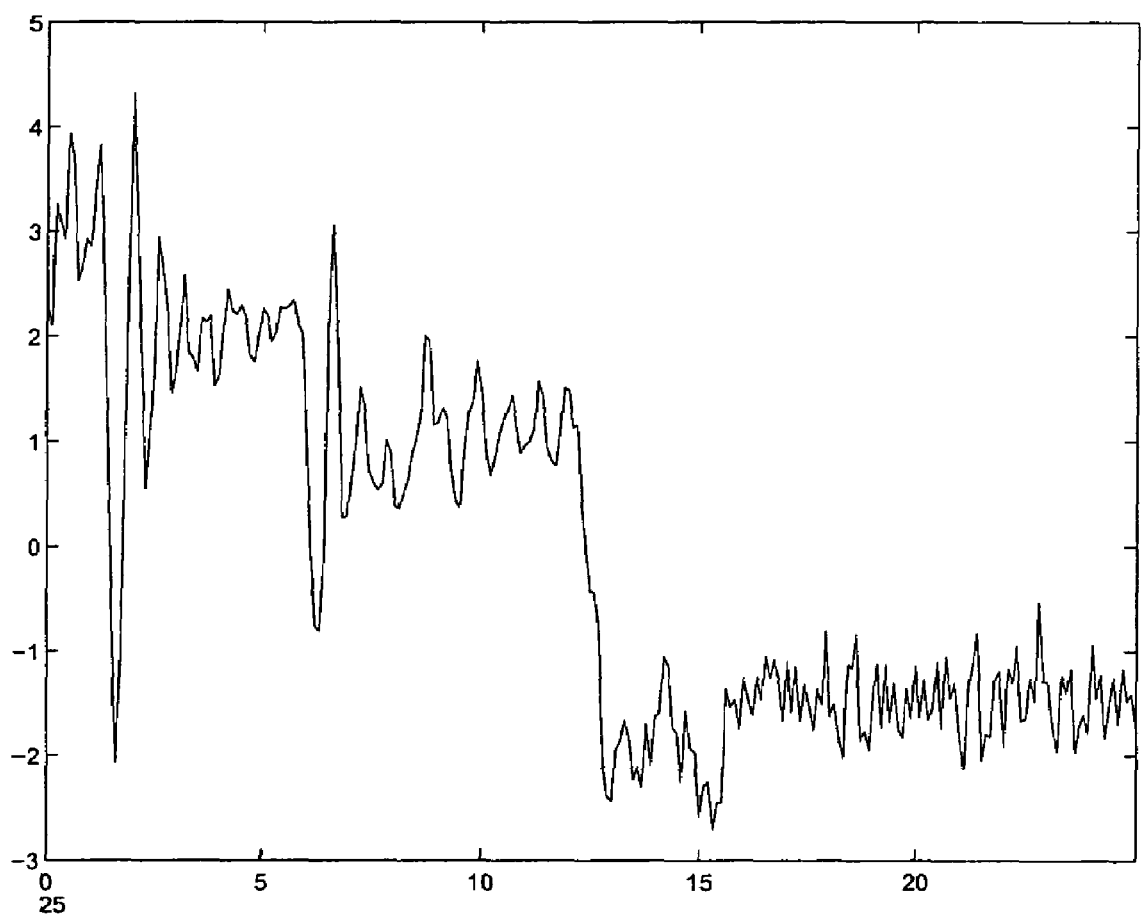

FIG. 8 shows the tracking error (mm) which is the difference between the imaging aperture and the simulated actual bolus peak position.

Figure 9:
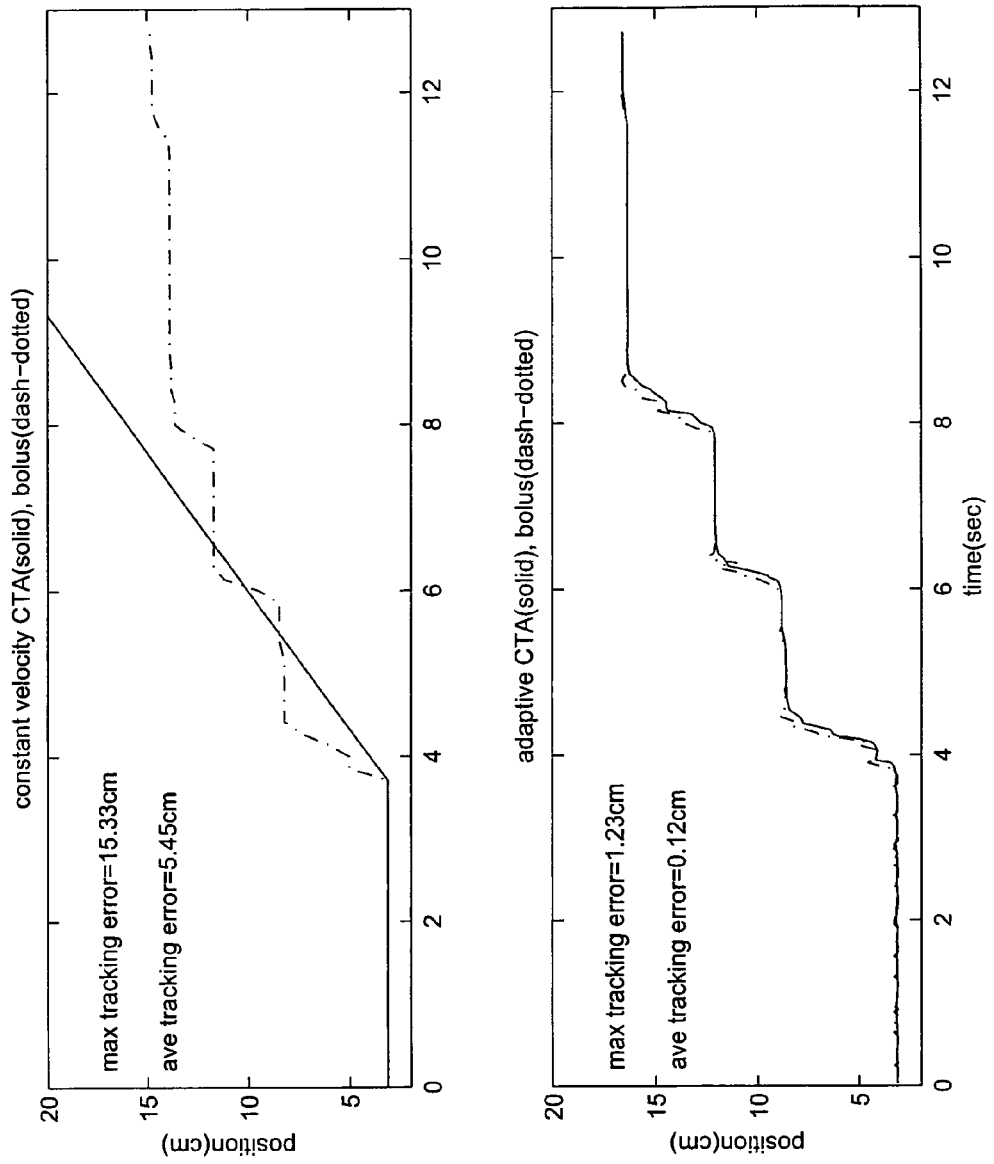

FIG. 9 shows an example of the actual bolus positon obtained clinically (dash-dotted line) and the controlled table postion (solid line).

Figure 10:
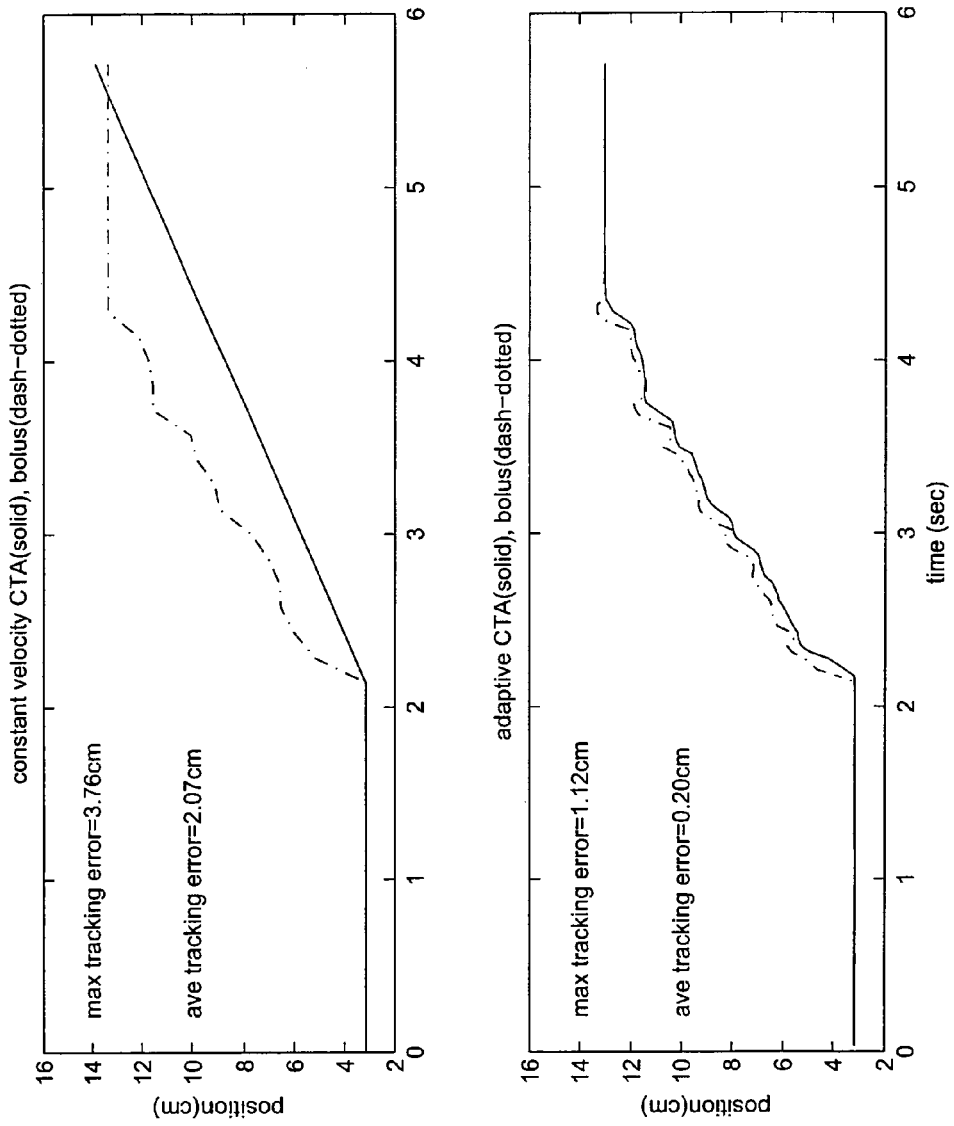

FIG. 10 shows another example of the actual bolus positon obtained clinically (dash-dotted line) and the controlled table postion (solid line).

DETAILED DESCRIPTION

The present invention is more particularly described in the following description and examples that are intended as illustrative only since numerous modifications and variations therein will be apparent to those skilled in the art. As used in the specification and in the claims, "a," "an," and "the" can mean one or more, depending upon the context in which it is used. The system and method are now described with reference to the Figures, in which like numbers indicate like parts throughout the Figures.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint the term.

"Optional" or "optionally" means that the subsequently described event or circumstance may or may not occur, and that the description includes instances where said event or circumstance occurs and instances where it does not.

By a "subject" or "patient" is meant an individual. The term subject or patient includes small or laboratory animals as well as primates, including humans. The term does not denote a particular age or sex. As used herein, "biological structure" includes a human or animal subject, or anatomical portions thereof.

The present invention can be utilized to provide adaptive bolus chasing CT angiography. The bolus-chasing problem is akin to that of tracking an airplane by radar. The difference is that bolus dynamics are much more complicated than the movement of an airplane. To follow an airplane, the next position of the airplane has to be estimated and predicted based on the current and previous positions of the airplane. In addition to prediction, the present invention consists of a control phase, i.e., once the next bolus position is predicted, the relative position of an imaging device and a biological structure being imaged can be adaptively adjusted to chase the motion of a bolus in the biological structure. For example, the imaging device can comprise a patient table and gantry, as is typical to current CT systems, and the patient table and/or gantry can be moved accordingly so that the bolus position and the imaging aperture of the imaging device are synchronized.

Bolus propagation is governed by a set of partial differential equations which contains a large number of patient and circulatory stage-dependent parameters. The full model of bolus propagation is fairly accurate provided that all parameters are available. Because these parameters are unknown, however, the full model has a little use in practice for adaptive bolus chasing CT angiography. Moreover, partial differential equations are not easy to use in practice and online estimation of such a large number of parameters in a very short time (typically CT angiography lasts about 20-30 seconds) is impossible.

Another commonly used model to describe bolus dynamics is the compartmental model that is also of little use for adaptive bolus chasing CT angiography. Again, the model is a set of equations involving a large number of unknown parameters that are patient and circulatory stage dependent. Obviously, parameters about the patient conditions, e.g., vessel radius at each stage of the vascular tree, are difficult to have in advance. Also, disease-state related parameters are impossible to be quantified prior to an angiogram. Further, the compartmental model describes contrast enhancement specific to a compartment (organ or vessel) instead of predicting the bolus dynamic as a function of time.

Since these models of the bolus dynamics are impractical, the system and method of chasing a bolus in a patient described herein is based on a simplified target model. One exemplary simplified target model that can be used is a simplified nonlinear model. For example, an extended Hammerstein model, which incorporates some of a patient's physiological parameters obtained on-line or off-line, can be used. A second exemplary simplified target model that can be used is a non-parametric model. A third exemplary simplified target model is a descriptive model.

These models predict bolus location based on available current and past bolus information, which can be obtained by real time imaging using a tomographic or other imaging system before the bolus arrives at its next (future) position. Using the predicted bolus location a controller can be used to adaptively adjust the relative position of the imaging device and the biological structure to chase the motion of the bolus. For example, the table and/or the gantry of an imaging device can be translated accordingly to capture image data. In this way, the bolus is chased by the imaging aperture to capture an optimal image. The simplified but target model (simplified target model) captures not every detail of the bolus dynamics but the key components including the bolus peak position and velocity.

By the adaptive control of the table/gantry motion, a variable pitch multi-slice/cone-beam scanning mode can be implemented. To perform the multi-slice/cone-beam CT angiography optimally, the pre-source collimator may be dynamically controlled longitudinally and/or transversely. This variable collimation mechanism reduces the radiation dose to the patient significantly.

The disclosed system and method include a bolus propagation model, a controller and an estimator/predictor. The model approximately reflects the bolus motion. The estimator/predictor estimates some parameters used in the model and computes the future position based on the model. The controller minimizes the discrepancy between the bolus peak position and the imaging aperture by synchronizing the bolus motion and the table/gantry translation.

The disclosed methods can be performed by an adaptive CT angiography system that can include hardware and software. The system and method are directed towards optimization of contrast enhancement utilizing (1) a simplified target model, for example, an extended Hammerstein model, or (2) a non-parametric model, which can be applied to CT angiography (CTA) that relies on bolus peak prediction, real-time CT observation and adaptive table/gantry transport or (3) a descriptive model which can be used with expert, fuzzy and intelligent controls.

The system and method can be applied to digital subtraction angiography (DSA), as well as other applications. For example, the bolus propagation modeling and imaging techniques of the present invention may be applied to arterial phase imaging of the liver and pancreas, and venous imaging of vital organs. These techniques may also be used for functional studies, such as cardiac motion and organ perfusion analysis.

A discrepancy, if any, can be reconciled between the predicted peak position of the bolus and the image data of the bolus to determine control actions. Because of a simplified target model is used, advanced control schemes, including robust, adaptive, optimal, expert, fuzzy and intelligent controllers, can be implemented.

Given a poorly known approximate individualized model of contrast bolus dynamics, the contrast wave peak may be locked in with a moving plane, slab and volume to depict anatomical/physiological/pathological features, based on interactions among real-time imaging based analysis, on-line estimation and robust control. In other words, the present invention targets a most important dynamic process in projective/tomographic imaging-contrast enhancement.

Figure 1:
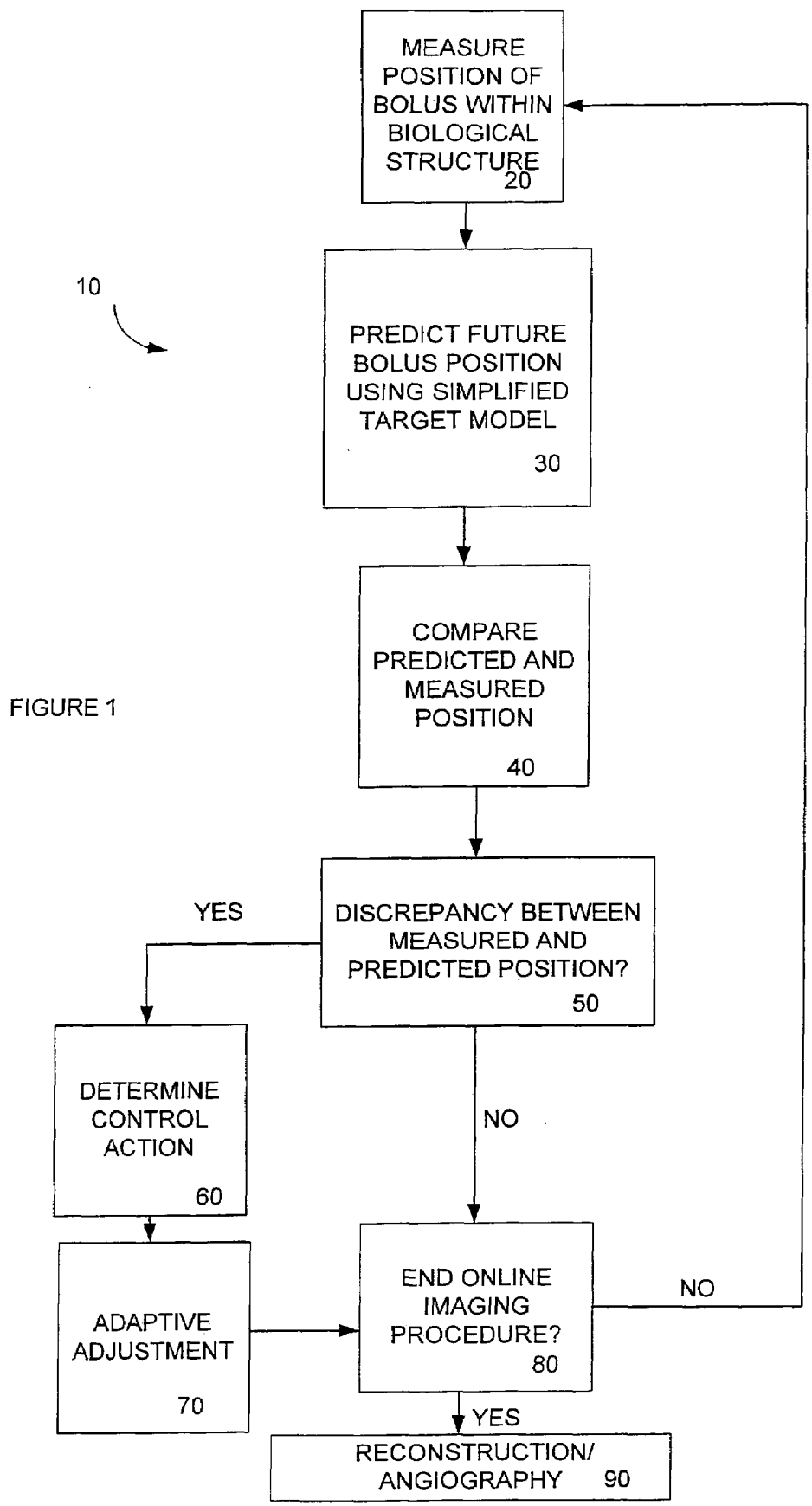
FIG. 1 is a block diagram illustrating an exemplary method of the present invention.

FIG. 1 is a block diagram illustrating an exemplary method 10 of utilizing bolus propagation and control for contrast enhancement comprising measuring with an imaging device a position of a bolus moving along a path in a biological structure 20. A future position of the bolus is predicted using a simplified target model 30 and compared with the measured position of the bolus 40. A control action is determined 60 to eliminate a discrepancy, if any, between the predicted position of the bolus and the measured position of the bolus 50. The relative position of the imaging device and the biological structure are adaptively adjusted according to the control action 70 to chase the motion of the bolus. At block 80, it is determined whether to end the imaging procedure. Such a determination can be made after adaptive adjustment at block 70, or if no discrepancy was identified between the measured and predicted position, at block 50. If it is determined that the imaging procedure is to end, then reconstruction and angiography can be preformed in block 90. If it is determined that the imaging procedure is not to end, then the position of the bolus can be measured within the biological structure at block 20.

The disclosed method can be practiced on a subject or a biological structure positioned on a table. For example, the biological structure may be placed on the table of an imaging device such as a CT scanner. The table of such a CT scanner is typically surrounded by a gantry which houses an imaging aperture. When the biological structure or subject is positioned on a table, the relative position of the imaging device and the biological structure can be adaptively adjusted according to the control action to chase the motion of the bolus by adaptively transporting the table on which the biological structure is positioned according to the control action. The relative position of the imaging device and the biological structure can also be adaptively adjusted according to the control action to chase the motion of the bolus by adaptively transporting the gantry surrounding a table on which the biological structure is positioned according to the control action. Moreover, both the gantry and the table can be adaptively transported to adaptively adjusting the relative position of the imaging device and the biological structure according to the control action.

In one aspect, the system and method relates to a computer-readable, digital storage device storing executable instructions which cause a processor to utilize bolus propagation for CT angiography in a biological structure for measuring with an imaging device a position of a bolus moving along a path in a biological structure and for predicting a future position of the bolus using a simplified target model. A simplified target model includes but is not limited to determining a (1) simplified nonlinear model, for example, an extended Hammerstein model, (2) a non-parametric model with a set of parameters prior to the arrival of the bolus at a location of the path (the parameters may be identified/estimated on-line), or (3) a descriptive model such as a fuzzy or rule based model. The predicted position of the bolus is compared with the image data associated with or indicating the measured position of the bolus and a control action is determined to eliminate a discrepancy, if any, between the predicted position of the bolus and the measured position of the bolus. Thus, the predicted and measured position of the bolus from the image data can be used to extrapolate a set of control parameters or a control action to eliminate the discrepancy. The relative position of the imaging device and the biological structure can be adaptively adjusted according to the control action to chase the motion of the bolus. Also provided herein is a computer readable medium having computer readable program code for utilizing bolus propagation and control for contrast enhancement. Such a computer readable medium comprises program code for measuring with an imaging device a position of a bolus moving along a path in a biological structure, for predicting a future position of the bolus using a simplified target model, for comparing the predicted future position of the bolus with the measured position of the bolus, for determining a control action to eliminate a discrepancy, if any, between the predicted position of the bolus and the measured position of the bolus, and for adaptively adjusting the relative position of the imaging device and the biological structure according to the control action to chase the motion of the bolus.

The methods described above can further comprise performing digital subtraction angiography. In a further aspect of the system and method, real-time estimation/prediction and measurement of bolus position is much more precise and comprehensive than relatively straightforward estimation and observation of bolus propagation in current 2D X-ray and MR DSA. In the present invention, bolus chasing may be based on bolus propagation prediction and monitoring, and may be performed continuously and optimally. In other words, the current limitations of bolus chasing imaging of prior art technology (which is "no automatic feedback loop") may be drastically improved by coupling advanced control and imaging methods with state of the art apparati.

Further provided herein is a system for utilizing bolus propagation and control for contrast enhancement comprising an imaging device for measuring a position of a bolus moving along a path in a biological structure. The system further comprises a predictor comprising a processor programmed for predicting a future position of the bolus using a simplified target model, a processor programmed for comparing the predicted future position of the bolus with the measured position of the bolus, and a controller comprising a processor programmed for determining a control action to eliminate a discrepancy, if any, between the predicted position of the bolus and the measured position of the bolus. The system also comprises an actuator for adaptively adjusting the relative position of the imaging device and the biological structure according to the control action to chase the motion of the bolus. The disclosed system can be used for performing the methods disclosed herein. Moreover, as would be clear to one skilled in the art, although the system is described having components including a predictor, processor for comparison, and controller, each comprising a processor, that a one or more processors could be used to perform these functions of the system. Thus, one or any combination of processors can be used in the system for the predictor, comparison processor, and controller.

Simplified Target Models

For the disclosed system and methods, an accurate estimation and prediction of the future bolus position based on the current and past bolus information can be determined. Modeling is an important step in estimating and predicting the bolus position. It has been shown that the full model of bolus propagation is governed by a set of very large number of partial differential equations that are however too complex and impractical. To overcome the difficulties of the full model, a simplified target model is used.

A simplified target model can determine the predicted position of the bolus based on current and past bolus positions and velocities. The current and past bolus positions and velocities can be provided by imaging reconstruction algorithms. Imaging algorithms are know to those skilled in the art and can be based on image domain and/or projection domain analyses. The image domain approach uses images reconstructed using an appropriate CT algorithm, such as approximate or exact spiral/helical CT algorithms, for example approximate circular cone-beam algorithms. The projection domain approach may also effectively identify the contrast change rate, for example, via conversion from cone-beam data in to Radon data before checking for the difference in the Radon space.

As described above, simplified target models that can be used include, but are not limited to, (1) a non-parametric model with a set of parameters prior to the arrival of the bolus at a location of the path, (2) a nonlinear model, for example, an extended Hammerstein model, or (3) a descriptive model such as a fuzzy or rule based model.

Non-Parametric Models

One example of a simplified target model that can be used in the disclosed method is a non-parametric model. A non-parametric model is not parameterized by parameters. Such a model can take many forms for example a function, a table, a curve, or variables.

Though the bolus velocity varies greatly, with current computer and CT techniques known to those skilled in the art, the difference of the bolus at two consecutive sampling instances may be small provided that the sampling rate is high. In fact, the bolus velocity may be considered as a constant between two sampling instances if the sampling interval is small. With knowledge of the current bolus velocity, which is the difference between the current and the immediate past bolus positions divided by the sampling interval, the next (future) bolus peak position can be accurately predicted. To estimate the velocity, only one parameter, the bolus position at the current time that is patient and circulatory stage-dependent, needs to be estimated. Moreover, this information can be readily obtained in modern CT systems. Therefore, based on this very simple adaptive nonlinear model, the future bolus peak position can be estimated and predicted. The non-parametric model works well, in particular, in the diastole stages of the subject.

Though the bolus velocity $v(i\Delta t)$ depends on $i\Delta t$ and is unknown, with a very short sampling period $\Delta t$, two consecutive $v(i\Delta t)$ and $v((i-1)\Delta t)$ are very close and differ by only a very small amount. Suppose there exists a small $\delta > 0$ so that $$v((i-1)\Delta t) - v(i\Delta t) = \Delta_i, \; |\Delta_i| \leq \delta,$$

Now, let $\hat{v}(i\Delta t)$ and $\hat{p}_b(i\Delta t)$ denote the estimates of $v(i\Delta t)$ and $p_b(i\Delta t)$ at time $i\Delta t$, respectively, and define the adaptive estimation algorithm $$\hat{v}(i\Delta t) = \hat{v}((i-1)\Delta t) + \mu(p_b(i\Delta t) - p_b((i-1)\Delta t) + e_i - \hat{v}((i-1)\Delta t)\Delta t)\hat{p}_b((i+1)\Delta t) = p_b(i\Delta t) + \hat{v}(i\Delta t)\Delta t$$

where $\mu > 0$ is the gain. Since $p_b(i\Delta t)$ and $p_b(i-1)\Delta t)$ are measurements from an imaging device noises are unavoidable denoted by $e_i$.

It can be mathematically shown that the above algorithm is convergent, i.e., $\hat{p}_b(i\Delta t)$ converges to $p_b(i\Delta t)$ asymptotically if $e_i$ and $\delta$ are zero, and $\hat{p}_b(i\Delta t)$ and $p_b(i\Delta t)$ are close if $e_i$ and $\delta$ are not zero but small.

Thus, using an exemplary non-parametric model, the future position of the bolus can be predicted by estimating the future position by $\hat{p}_b((i+1)\Delta t) = p_b(i\Delta t) + \hat{v}(i\Delta t)\Delta t$, wherein $\hat{v}(i\Delta t)$ and $\hat{p}_b(i\Delta t)$ denote an estimate of the bolus velocity and position $v(i\Delta t)$ and $p_b(i\Delta t)$ at time $i\Delta t$, respectively. In this exemplary non-parametric model $p_b(i\Delta t) = p_b((i-1)\Delta t) + v((i-1)\Delta t)\Delta t$ and $\hat{v}(i\Delta t) = \hat{v}((i-1)\Delta t) + \mu[p_b(i\Delta t) - p_b((i-1)\Delta t) - \hat{v}((i-1)\Delta t)\Delta t]$. The imaging device or a portion thereof can be adaptively transported to $\hat{p}_b((i+1)\Delta t)$ at time $(i+1)\Delta t$ by setting $u(i\Delta t) = \hat{p}_b(i\Delta t + \Delta t)$ where $p_b(i\Delta t + \Delta t) = u(i\Delta t)$ and $u(i\Delta t)$ is the control action.

Extended Hammerstein Model

Another non-limiting example of a simplified target model that can be used is an extended Hammerstein model. The extended Hammerstein model can be an approximate linear model with some parameters entering nonlinearly. A Hammerstein model is a cascade of static nonlinearity followed by a dynamic linear system. An extended Hammerstein model is a Hammerstein model where the input to the nonlinearity can be multi-dimensional.

The idea is that within each body section, the bolus propagation can be approximately modeled by a linear system, provided that the pulsatility of the blood flow is not very strong. The extended Hammerstein model can take many different forms that can be used in the disclosed system and methods. Optionally, the extended Hammerstein model can be a dynamic nonlinear system followed by a linear dynamic system. The Extended Hammerstein Model disclosed herein is exemplary and is not intended to be limiting.

At a fixed location y, the bolus dynamics can be described by convolutions of three functions $$b(t, y) = c(t) * \frac{1}{\sigma(y)\sqrt{2\pi}} e^{-\frac{(t-t_c(y))^2}{2\sigma^2(y)}} * \frac{1}{\tau(y)} e^{\frac{t}{\tau(y)}}$$

where the function c(t) is determined by the injection of the bolus and the parameters $t_c$, $\tau$ and $\sigma$ depend on the location y, i.e., the body section.

The overall system is a nonlinear system that consists of several linear systems which switch from one to another depending on the body section. If the body is divided into three sections, the extended Hammerstein model consists of three linear systems b(t, y$_1$), b(t, y$_2$), b(t, y$_3$)

for y≠y$_1$, y$_2$, y$_3$ b(t, y) can be obtained by interpolation or extrapolation. The difference between this model and the traditional Hammerstein model is that the nonlinearity acts like a switching function depending on external conditions. If the parameters $\sigma$, $\tau$ and $t_c$ can be estimated, the complete dynamics of the bolus is available and in turn, the next bolus peak position is obtained. In the case that the pulsatility is strong, the models can be separated from the systole phase to the diastole phase. Then, additional EKG signal are used.

In the aortic areas of a subject during the systole stages the bolus velocity surges and this sudden jump may cause some tracking errors. To this end, a nonlinear (extended Hammerstein) model can be used which predicts the surges of the bolus. Let s(i) denote the S phase of the ith ECG signal, the idea of the nonlinear model can be described as $$\hat{p}_b(k\Delta t + dt) = \begin{cases} p_b(k\Delta t) & s(i) + q(i) \leq k \leq s(i+1) \\ p_b(k\Delta t) + c & s(i) = k < s(i) + q(i) \end{cases}$$

for some tunable variables q(i) and c, where c captures the jumps of the bolus velocity during the systole stages. After a small time interval q(i), the bolus becomes stationary again.

Thus, using an exemplary extended Hammerstein model the future position of the bolus can be predicted by estimating the parameters $\sigma$, $\tau$ and $t_c$ wherein the movement of the bolus is described by $$b(t, y) = c(t) * \frac{1}{\sigma(y)\sqrt{2\pi}} e^{-\frac{(t-t_c(y))^2}{2\sigma^2(y)}} * \frac{1}{\tau(y)} e^{\frac{t}{\tau(y)}}$$

and wherein the function c(t) is determined by the injection of a bolus into a subject and the parameters $t_c$, $\tau$ and $\sigma$ depend on a location y within the subject. The exemplary extended Hammerstein model can comprise three linear systems b(t, y$_1$), b(t, y$_2$), b(t, y$_3$) and y≠y$_1$, y$_2$, y$_3$, b(t, y) can be obtained by interpolation or by extrapolation.

If an extended Hammerstein model is used, individualized parameter can be input into the model. The individualized parameter that can be input include but are not limited to an ECG signal, heart rate, rhythm, stroke volume, contractility, cardiac preload and cardiac afterload. These parameters are physiological parameters of the biological structure, or physiologically dependent parameters of the biological structure.

Adaptive estimation/identification algorithms can be used to estimate parameters that may not be directly measurable such as bolus dispersion, which allows for the continuous update of the parameter estimates. Continuous updating improves the quality of prediction and control based on recently collected observations. Therefore, the disclosed system and method significantly improves tomographic angiography.

Optionally, an ECG signal is input into the extended Hammerstein model to predict a surge of the bolus during a systole stage of a subject's cardiac cycle. As described above, the exemplary extended Hammerstein model can be described by $$\hat{p}_b(i\Delta t + \Delta t) = \begin{cases} p_b(i\Delta t) & s(k) + q(k) \leq i \leq s(k+1) \\ p_b(i\Delta t) + c & s(k) = i < s(k) + q(k) \end{cases}$$

for some q(k) and c, where c captures the surge of the bolus during the systole stage and s(k) denotes the S phase of a kth ECG signal.

Descriptive Models

A third non-limiting example of a simplified target model that can be used in the described methods is a descriptive model. A rule based model represents a system involving rules reminiscent of a human describing a system. Optionally, the descriptive model is a fuzzy model or a rule based model. This type of model is very well suited for rule based controllers, e.g., expert, fuzzy and intelligent controls.

Estimator/Estimation

An estimator can be used to estimate patient or subject dependent parameters embedded in a model using adaptive estimation algorithms known in the art that include, but are not limited to the Least squares algorithms, the LMS algorithms and the variable gain algorithm. Once these parameters become available, the predictor predicts the future bolus peak position and shape.

Controllers/Control

The simplified target model approximately reflects the bolus motion. The estimator can be used to estimate parameters used in the model and the predictor computes the future position based on the model. The controller can be used to minimize the discrepancy between the bolus peak positions and the imaging aperture by synchronizing the bolus motion and the table/gantry translation. In implementation, however, some parts can be combined.

As described above, the imaging device used can comprises a table and a gantry surrounding the table and the determined control action can define the amount, direction and velocity to adaptively transport the table or the gantry surrounding the table to chase the motion of the bolus. The control action can be determined by a control law which can be selectable by a user. The control law may include, but is not limited to, PID controls, optimal controls, H_inf controls, robust controls, adaptive controls, LQR, expert controls, fuzzy controls, and intelligent controls. Choice of control laws depends on the application and can be selected by one skilled in the art. For example, if the maximum tracking error is to be minimized, H_inf control can be selected. In another example, if average tracking error is to be minimized, LQR control can be selected. For rule based models, fuzzy or expert controls can be selected. The table and/or gantry surrounding the table can be adaptively transported by an actuator that moves the table or gantry surrounding the table according to the determined control action.

The control action or the set of control parameters can be delivered to a control unit or controller can be used to adaptively adjust the relative position of the imaging device and the biological structure to chase the motion of the bolus.

For example, the table and/or the gantry of an imaging device can be translated accordingly to capture image data. The controllers can move the patient table and/or the gantry by the exact amount as the bolus peak in the same or opposite directions so that the bolus peak position and the imaging aperture are synchronized. The controllers comprise two parts. The first part determines what control action should be taken and by how much the patient table/the gantry should be moved. This part depends on types of control laws adopted, e.g., robust, optimal, fuzzy and others. The second part is an actuator that moves the patient table and/or the gantry by the exact amount and the direction as determined by the control law so that the bolus peak position and the imaging aperture are synchronized.

The control system can be conceptually viewed as comprising an imager, a predictor, an estimator and an actuator. An imager or imaging acquiring, processing and re-construction: This component provides real time bolus position and shape. A predictor: Based on a priori bolus dynamics model and observed measurements, it predicts future bolus positions and shapes. Since the bolus dynamics depends on individual patient conditions, the model inevitably involves some unknown parameters. An estimator: The estimator component estimates unknown parameters on-line based on the measurements. Different estimation/identification algorithms may be applied, for instance, the least squares algorithm, the LMS algorithm and the variable gain algorithm. An actuator: The actuator component is the patient table and/or the gantry controlled by a motor. The motor takes information from the predictor and moves the table and/or the gantry so that the imaging aperture and the bolus are synchronized. The control scheme can be PID, adaptive, optimal, robust or others, as described above.

Thus, both the CT table and the bolus dynamics are involved. For the CT table, most existing control systems use an AC or DC motor serve system to move the table. If a stepping motor system is used, the mathematical equation that describes the CT table motion is surprisingly simple provided that the motor has enough torque. Let $\Delta t$ be the sampling interval and $p_T(i\Delta t)$ be the table position at time $i\Delta t$. The table position at time $i\Delta t+\Delta t$ is given by $$p_T(i\Delta t+\Delta t)=u(i\Delta t)$$

where $u(i\Delta t)$ is the control input at our disposal at time $i\Delta t$ to the motor serve system informing the stepping motor how many revolutions it should turn that translates into the table linear distance. If the bolus peak position $p_b(i\Delta t+\Delta t)$ were available at time $i\Delta t$, one could set $$u(i\Delta t)=p_b(i\Delta t+\Delta t)$$

that guarantees $$p_T(i\Delta t+\Delta t)=p_b(i\Delta t+\Delta t)$$

a perfect synchronization between the bolus peak position and the imaging aperture. This would solve the adaptive control problem. The future bolus peak position $p_b(i\Delta t+\Delta t)$ is however unknown at time $i\Delta t$, and a simplified target model is used to estimate and predict the future bolus peak position.

An accurate estimation and prediction of the future bolus peak position $p_b(i\Delta t+\Delta t)$ based on the current and past bolus information $p_b(k\Delta t)$, $k \leq i$ can be made.

Let $p_i=p(i\Delta t)$ be the bolus position at time t and $v_i=v(i\Delta t)$ be the average velocity of the bolus between two consecutive sampling instances t and $t+\Delta t$, where $\Delta t$ is the sampling period. Accordingly, $$p_{i+1}=p_i+v_i\Delta t$$

Should the bolus position $p_{i+1}$ at time $(i+1)\Delta t$ be available in advance at time $i\Delta t$, the control would become relatively easy, i.e., to move the patient table to $p_{i+1}$ at time $(i+1)\Delta t$. $p_{i+1}$ is unknown at time $i\Delta t$ and can be estimated based on $p_k$'s and $v_k$'s, $k \leq i$, or their estimates.

Figure 2:
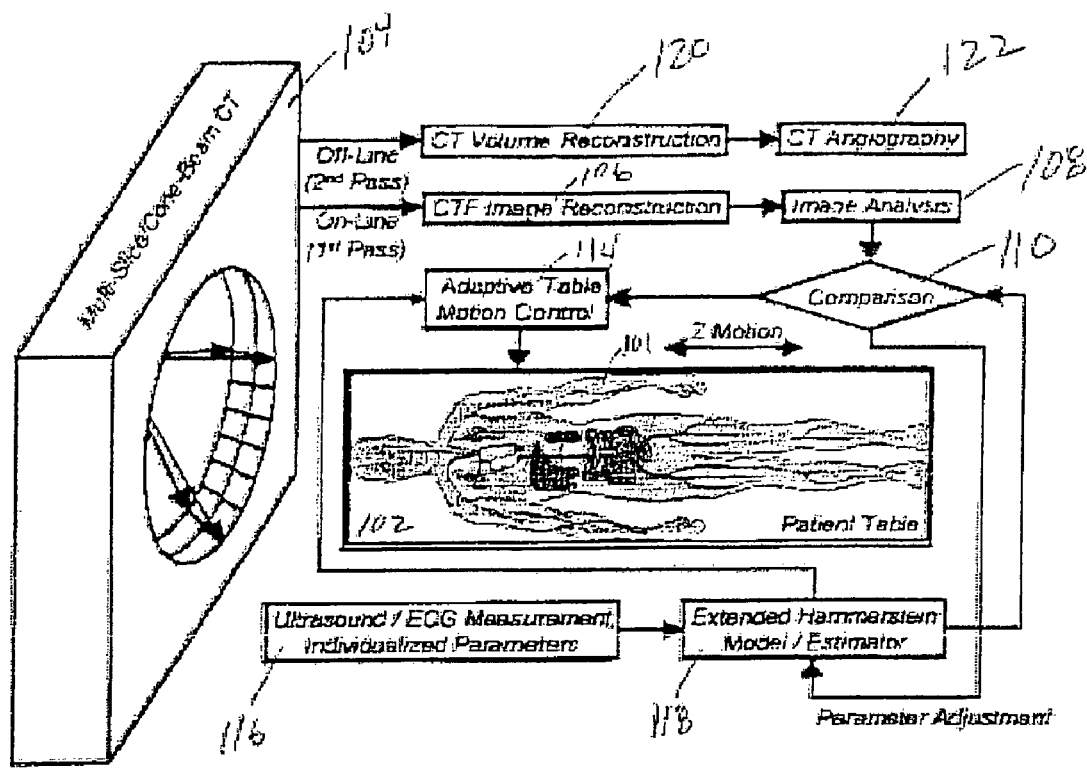
FIG. 2 is a schematic diagram illustrating an exemplary method of utilizing bolus propagation for adaptive CT angiography according to one aspect of the present invention.

The present invention can be utilized to provide adaptive bolus chasing CT angiography. FIG. 2 shows a method 100 of utilizing bolus propagation for adaptive CT angiography according to one aspect of the present invention. Currently, when a CT angiography is performed on a patient 101, the patient is positioned on a patient table 102. A bolus (not shown) is introduced into the patient 101 and can be monitored by CT fluoroscopy ("CTF") and other imaging techniques. The images can be obtained by a spiral CT scanner 104 in single-slice, multi-slice or cone-beam configurations, in which case the patient 101 is scanned by the scanner 104. The issue is how to better monitor and chase the dynamic propagation of the bolus inside the body of the patient 101.

This approach using an exemplary simplified nonlinear model is illustrated graphically in FIG. 2. A similar approach can be used with an alternative simplified target model, such as a non-parametric or a descriptive model. Initially, a patient 101 is positioned at the patient table 102 and a bolus is injected into the patient 101 to move along a path in the blood circulatory system of the patient. At step 102, bolus position is monitored by CTF or other imaging techniques performed on the CT scanner 104. At step 106, on-line image reconstruction is performed. At step 108, real-time image analysis is performed to produce images for the measured bolus position. In parallel, if a simplified nonlinear model is used, at step 116, a set of individualized anatomical and physiological parameters can be provided, measured or estimated on-line. These include, but are not limited to EKG readings, heart rate (HR), rhythm, stroke volume (SV), contractility (dl/dt), and cardiac pre-load and after-load. Such information is part of the Extended Hammerstein model so that the bolus position can be better estimated and predicted.

At step 118, a predicted bolus position prior to the arrival of the bolus at a location can be calculated by the model using input of estimated current and past bolus velocities and positions based on the estimator/predictor. The estimator and predictor use adaptive estimation algorithms that include, but not limited to the Least squares algorithms, the LMS algorithms and the variable gain algorithm. The estimator is especially important for the Hammerstein model which consists of unknown parameters. These unknown parameters, which can include, but are not limited to those described above, can be provided by additional signals including, for example, a patient's EKG signals. When these parameters are estimated, the model can be used to more accurately predict next bolus position. If a nonparametric model is used, predicted bolus position can be calculated without input of these additional parameters.

At step 110, the predicted position of the bolus from step 118 and the imaging aperture position are compared. At step 114, discrepancy, if any, between the predicted position of the bolus and the imaging aperture position, is compensated by a controller which moves the patient table and/or the CT gantry accordingly so that the peak bolus position and the imaging aperture are synchronized. At step 114, the controller takes input information from steps 118 and 110, and controls the patient's table and/or the CT gantry accordingly. Control designs that can be used include, but are not limited to, PID controls, optimal controls, H_inf or other robust controls and adaptive controls known to those skilled in the art. This process of comparison 110 and compensation 114 with input from steps 118 and 110 is dynamic and can be repeated until part or all points of the interest along the path in the blood circulatory system of the patient have been imaged. Moreover, the number of variables used in the Extended Hammerstein Model at step 118 can be adjusted during the process by information gained from images for the measured bolus position at step 108. At step 120, after the CTF is performed or the scan is done on the patient, the off-line CT volume reconstruction is performed 120. At step 122, CT angiography is conducted.

Figure 3:
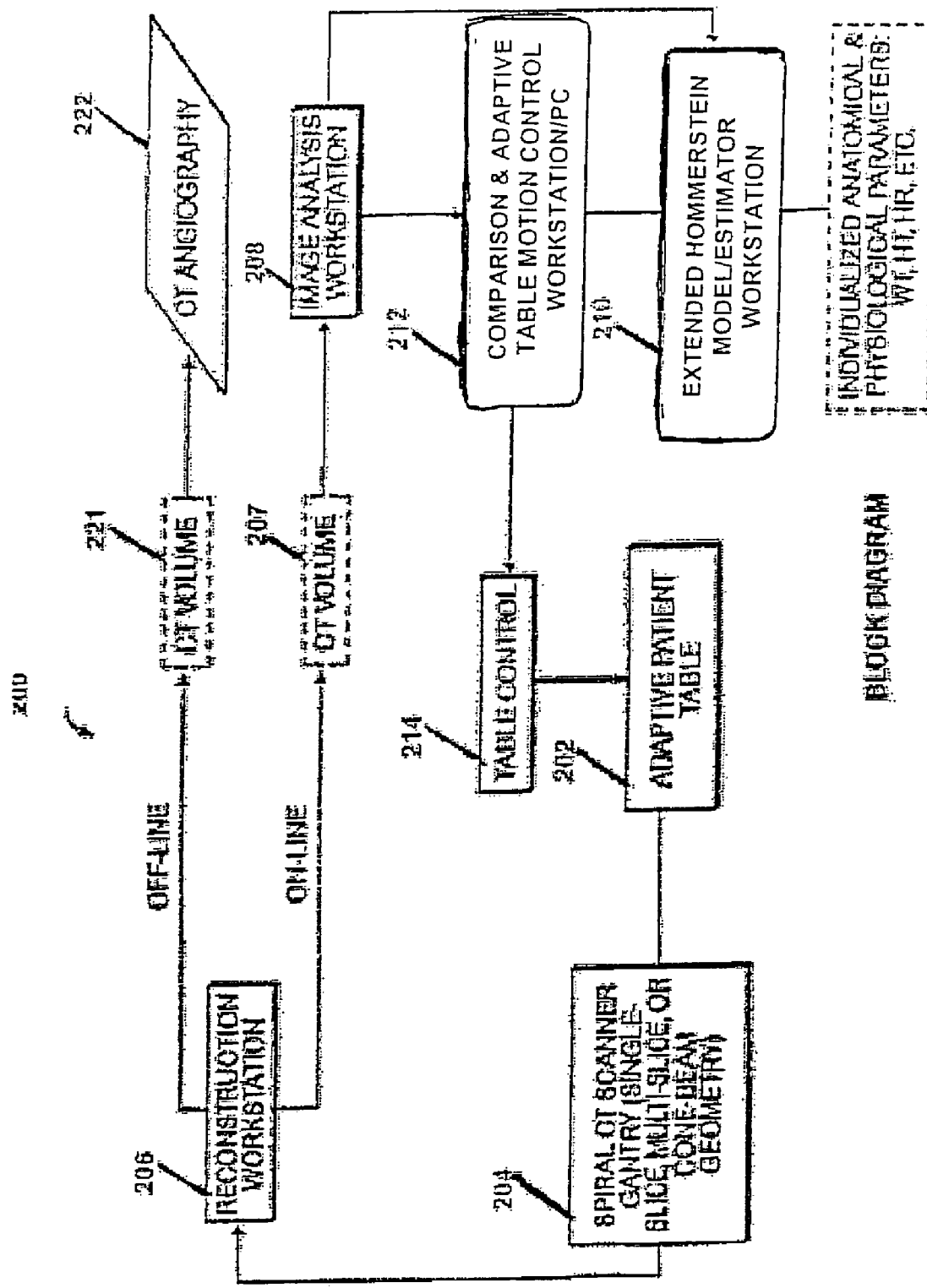
FIG. 3 is a system diagram depicting an exemplary adaptive CT angiography system for performing the method depicted in FIGS. 1 and 2 according to one embodiment of the present invention.

The method 100 according to the present invention can be performed by an adaptive CT angiography system which can have hardware and software. One such system 200 according to one embodiment of the present invention is shown in FIG. 3. The system 200 includes a patient table 202 for supporting a patient (not shown). The patient table 202 is adaptive to table control 214. The system 200 has a monitoring device 204 such as a spiral CT scanner to monitor the patient on the patient table 202, in particular, to monitor the propagation of a bolus (not shown) that is injected into the patient. Scanning can be performed in single slice, multi-slice, or cone-beam geometry. The system 200 also has a reconstruction workstation 206 coupled to the monitoring device 204, a workstation 208 coupled to the reconstruction workstation 206, a comparison and adaptive table motion control workstation/personal computer ("PC") 212 coupled to the workstation 208, and a workstation 210 coupled to comparison and workstation/PC 212, where the workstations 208 and 210 can also communicate to each other. The workstation 206 can perform on-line CTF image construction, as described above for step 106, and provide CTF images to the workstation 208 to conduct image analysis, as described above for step 108. The workstation 208 performs image analysis and outputs the results to comparison and workstation/PC 212, and to workstation 210 for adjusting parameters to be used in the Extended Hammerstein Model/Estimator. The workstation 210 receives a set of parameters such as individualized anatomical and physiological parameters on-line and/or off-line and building Extended Hammerstein Model, a non-parametric model, or a descriptive model. Then, based on the model, the next bolus position prior to the arrival of the bolus is estimated and predicted. The parameters utilized in the bolus propagation model can be adjusted by the workstation 210 using the results of image analysis from the workstation 208. Workstation/PC 212 reconciles discrepancy, if any, between the predicted position of the bolus and the measured bolus position by a controller. The controller acts when the new information from the model and the estimator becomes available. The workstation 206 also performs off-line CT volume reconstruction to provide CT volume 221 for CT angiography 222. It is important to note that the above illustration only considers table control. In fact, table control can be changed to gantry control or combined table and gantry controls.

While the system 200 as shown in FIG. 3 has a plurality of workstations or computers, it can have more or less workstations. Indeed, the functions performed by workstation 206, workstation 208, workstation/PC 212, and workstation 210 can be performed by just one workstation or computer having a processor that has proper memory, speed and power. Moreover, even if more than one workstations or computers are utilized a different configuration than the one given in FIG. 3 may be used to practice the present invention.

Figure 4:
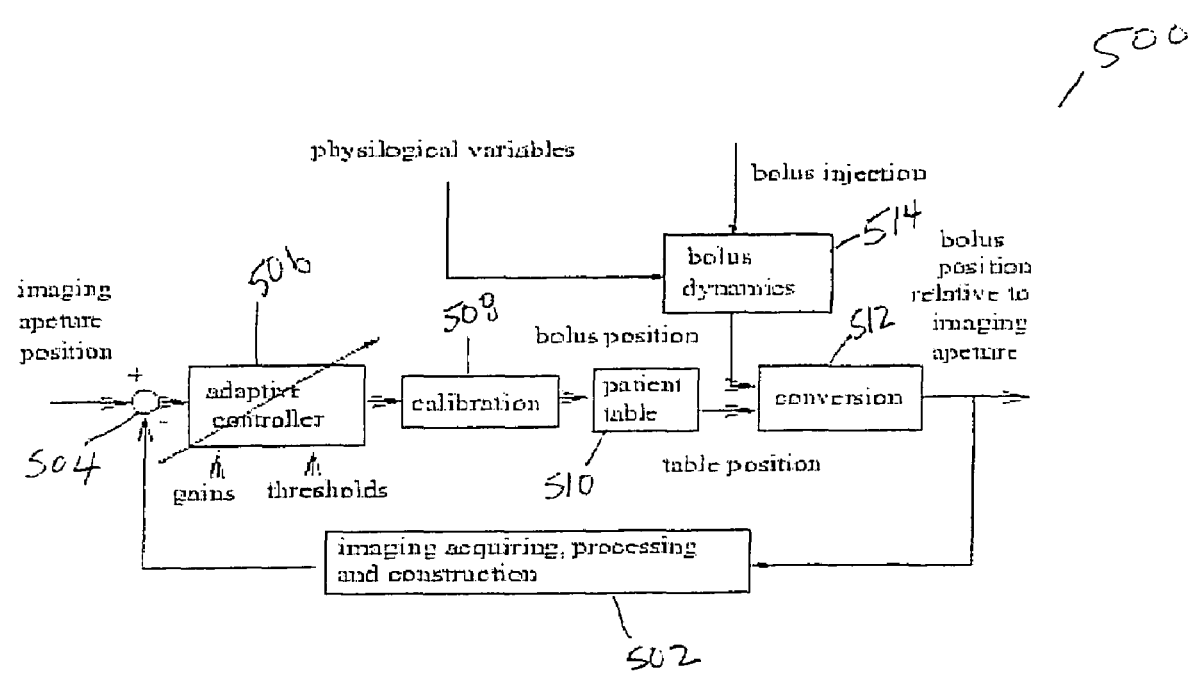
FIG. 4 is a schematic diagram depicting an exemplary adaptive CT angiography system using a non-parametric model according to one embodiment of the present invention.

A non-parametric model and an LMS algorithm can be implemented. The system according to one embodiment of the invention is shown in FIG. 4. The system 500 includes an imager 502 that comprises imaging acquiring, processing and construction using the NI Labview software which is widely available, an adaptive controller 506 that comprises an estimator/predictor using the LMS algorithm and a patient table 510 comprising a table and an actuator which is a stepping motor.

A patient (not shown) is positioned at the patient table 510 and a bolus is injected (not shown). The bolus position is monitored on-line by the imager 502. At 504, the positions of the bolus and the imaging aperture are compared and the difference is fed into adaptive controllers 506. The adaptive controller 506 also stores current and past bolus information to predict future bolus position. There are several adjustable parameters, e.g., gains and thresholds that can be inputs into 506. Because the position at 506 is calculated in terms of pixie, calibration 508 translates the distance from pixie to numbers of revolutions necessary for the stepping motor that is part of 510.

At 510, the motor moves the patient table by the amount given by the output of 508. The bolus dynamics 514 represents unknown bolus dynamics that depends on bolus inject patterns and individual physiological conditions. Now, the difference between the bolus position and the imaging aperture is in terms of meters, the block 512 converts the actual distance into pixie used in the imaging processing. Since the model is non-parametric, there is no link from physiological variables to the block of adaptive controller. There is a link, however, if an extended Hammerstein model is adopted.

EXAMPLES

Example 1

Adaptive bolus chasing angiography was performed in a computer simulated clinical environment based on published values of blood velocities as shown in Table 1.

TABLE 1

|  | Peak Velocity (cm/s) | Mean Velocity (cm/s) | Diameter ± SD (cm) |
|---|---|---|---|
| Aorta (Ao) | 150 ± 30 | 27 ± 8.9 | 1.8 ± 0.2 |
| Common Iliac Artery (CIA) | 125 ± NA | 13.5 ± 4.0 | 0.9 ± NA |
| External Iliac Artery (EIA) | 119 ± 21.7 | 10.5 ± 5.0 | 0.79 ± 0.13 |
| Common Femoral Artery (CFA) | 114 ± 24.9 | 10.2 ± 4.8 | 0.82 ± 0.14 |
| Superficial Femoral Artery (SFA) | 90.8 ± 13.6 | 8.8 ± 3.5 | 0.60 ± 0.12 |

TABLE 1-continued

|  | Peak Velocity (cm/s) | Mean Velocity (cm/s) | Diameter ± SD (cm) |
|---|---|---|---|
| Popliteal Artery (PA) | 68.8 ± 3.5 | 4.9 ± 2.9 | 0.52 ± 0.11 |
| Posterior Tibial Artery (PTA) | 61 ± 20 | 4.4 ± 3.3 | 0.25 ± NA |
| Dorsalis Pedis Artery (DPA) | NA | 3.6 ± 3.8 | 0.2 ± NA |

Injected contrast bolus was modeled by the above data, future bolus position and shape were predicted based on online-estimated patient parameters, and the patient table was controlled so that the trans-axial imaging aperture was synchronized with the predicted bolus peak position. The mathematical detail of the model used is provided below.

Let t denote the current time and $\Delta t$ the sampling interval. In other words, $t-\Delta t$ and $t+\Delta t$ are the immediate past and next (future) sampling instants. Let p(t) & v(t) be the bolus peak position and velocity at time t, and $\hat{p}(t)$ & $\hat{v}(t)$ their estimates, respectively. The variable gain identification algorithm (Bai and Huang, Automatica 36:1001-1008 (2000)) to estimate the bolus peak velocity is defined as $$\hat{v}(t) = \hat{v}(t - \Delta t) + g(t)e(t)$$

with $$e(t) = p(t) - p(t - \Delta t) - \hat{v}(t - \Delta t)\Delta t$$

$$g(t) = \begin{cases} \mu & |e(t)| \geq \delta \\ \max\left[\left(1 - \frac{\delta}{|e(t)|}\right), \mu\right] & |e(t)| < \delta \end{cases},$$

where $\mu=\delta=0.1$, e(t) is the prediction error based on the previous estimate $\hat{v}(t-\Delta t)$ and g(t) is the gain of the algorithm. The algorithm has a very clear interpretation. If the previous estimate $\hat{v}(t-\Delta t)$ was accurate, then the error e(t)=0 and there is no need to update $\hat{v}(t)$. In this case, $\hat{v}(t)=\hat{v}(t-\Delta t)$. If e(t)≠0, then the previous estimate $\hat{v}(t-\Delta t)$ was inaccurate and needs to be adjusted. Two scenarios exist: 1) the error e(t) is large, and 2) the error e(t) is small. For large errors, a large gain g(t) is used to speed up the estimation rate, whereas for small errors a small adjustment g(t) is needed.

Once the estimate of the bolus velocity is obtained, it is used to predict the next (future) bolus peak position using the following equation $$\hat{p}(t+\Delta t) = p(t) + \hat{v}(t)\Delta t$$

where $\hat{p}(t+\Delta t)$ is predicted bolus peak position at time $t+\Delta t$ and $\hat{v}(t)$ is the current velocity estimate.

The patient table was moved according to the predicted bolus peak position so that the bolus peak position and the imaging aperture are synchronized. In simulations, the patient table dynamics is modeled as a standard direct current (DC) motor (Franklin et al., Feedback Control of Dynamic Systems 4th ed. (2002)). In control terminology, it is a second order transfer function. The control design is a classic closed loop system known to those skilled in the art (Franklin et al., Feedback Control of Dynamic Systems 4th ed. (2002)).

MATLAB (Version 6.3, The Mathworks, Inc., Natick, Mass.) was used for numerical calculations and simulations. The bolus propagation characteristics were modeled by piece-wise constants (solid line, FIG. 5) according to the published values of blood velocities in different regions of the vascular tree (Table 1).

The adaptive nonlinear model accurately estimated and predicted the "actual" bolus propagation under disease free physiologic conditions derived from the published data on blood velocity characteristics (FIGS. 5 and 6). With the predicted future bolus peak position, the controlled table position and "actual" bolus peak position were indistinguishable (FIGS. 5 and 6). In fact, the maximum error was less than 1 millimeter. In other words, synchronization between the bolus peak potion and the imaging aperture was achieved.

Example 2

A non-parametric model was implemented on a prototype CT scanner. This prototype consisted of a PC (personal computer), a Master Flex Pump 7550-30, a movable table controlled by a Vexta alpha stepping motor AS46 and a Pulnix-6700 camera. Plastic tubings configured similar to a patient's aorta and arteries were placed on the top of the table. The variable velocity pump was controlled by the PC and a patient's blood flow was stimulated by driving a bolus through plastic tubings. The velocity was assigned by a computer program. The camera, connected to the PC by a PCI card, provided the real time bolus position that simulated the CT imaging device. The imaging acquiring and processing were carried by NI IMAQ VISION DEVELOPMENT MODULES.

The model's algorithms were implemented by using the NI Labview software which is widely available. The stepping motor took commands from the PC through a serial port and controlled the table position, thereby simulating a patient table. The results using the prototype scanner are shown FIGS. 7 and 8. FIG. 7 shows the actual bolus peak position (solid line) and the controlled patient table position (dash-dotted line). FIG. 8 shows the tracking error (mm) which is the difference between the imaging aperture and the simulated bolus peak position. The maximum tracking error was within 4 mm.

Example 3

The above discussed scheme with a non-parametric model was also tested on actual bolus propagation data that were collected from more than 20 patients. FIGS. 9 and 10 show results of two tests. In the figures, the actual bolus peak positions collected from patients are described by dash-dotted lines. The top diagrams are the CT table positions in solid lines using the current constant velocity technology. The bottom diagrams are the CT table positions in solid lines using the scheme discussed in this patent. Clearly, the adaptive bolus chasing CTA performs satisfactorily.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Throughout this application, various publications are referenced. The disclosures of these publications in their entireties are hereby incorporated by reference into this application in order to more fully describe the compounds, compositions and methods described herein.

REFERENCES

Bai E W, Huang Y. Variable gain parameter estimation algorithms for fast tracking and smooth steady state. Automatica 2000; 36:1001-1008.

Franklin G F, Powell J D, Emami-Naeini A. Feedback Control of Dynamic Systems. In. 4th ed. Upper Saddle River, N.J.: Prentice-Hall; 2002.

Bennett, J, E. W. Bai, J. Halloran and G. Wang, A preliminary study on adaptive field of view tracking in peripheral digital subtraction angiography, J. of X-ray Science and Technology, 2003:11, 149-159

What is claimed is:

1. A method of utilizing bolus propagation and control for contrast enhancement comprising:
   measuring with an imaging device a position of a bolus moving along a path in a biological structure;
   predicting a future position of the bolus using a simplified target model, wherein the simplified target model is a non-parametric model and wherein predicting the future position of the bolus comprises estimating the future position by $\hat{p}_b((i+1)\Delta t) = p_b(i\Delta t) + \hat{v}(i\Delta t)\Delta t$, wherein $\hat{v}(i\Delta t)$ and $\hat{p}_b(i\Delta t)$ denote an estimate of the bolus velocity and position $v(i\Delta t)$ and $p_b(i\Delta t)$ at time $i\Delta t$, respectively;
   comparing the predicted future position of the bolus with the measured position of the bolus;
   determining a control action to eliminate a discrepancy, if any, between the predicted position of the bolus and the measured position of the bolus; and
   adaptively adjusting the relative position of the imaging device and the biological structure according to the control action to chase the motion of the bolus.

2. The method of claim 1, wherein adaptively adjusting the relative position of the imaging device and the biological structure according to the control action to chase the motion of the bolus comprises adaptively transporting a table on which the biological structure is positioned according to the control action.

3. The method of claim 1, wherein adaptively adjusting the relative position of the imaging device and the biological structure according to the control action to chase the motion of the bolus comprises adaptively transporting a gantry surrounding a table on which the biological structure is positioned according to the control action.

4. The method of claim 1, wherein adaptively adjusting the relative position of the imaging device and the biological structure according to the control action to chase the motion of the bolus comprises adaptively transporting a table on which the biological structure is positioned and transporting a gantry surrounding the table according to the control action.

5. The method of claim 1, wherein the simplified target model determines the predicted position of the bolus based on current and past bolus positions and bolus velocities.

6. The method of claim 5, wherein the current and past bolus positions and velocities are provided by imaging reconstruction algorithms.

7. The method of claim 1, wherein, $p_b(i\Delta t) = p_b((i-1)\Delta t) + v((i-1)\Delta t)\Delta t$.

8. The method of claim 1, wherein $\hat{v}(i\Delta t) = \hat{v}((i-1)\Delta t) + \mu[p_b(i\Delta t) - p_b((i-1)\Delta t) - \hat{v}((i-1)\Delta t)\Delta t]$.

9. The method of claim 1, wherein the imaging device or a portion thereof is adaptively transported to $\hat{p}_b((i+1)\Delta t)$ at time $(i+1)\Delta t$ by setting $u(i\Delta t) = \hat{p}_b(i\Delta t + \Delta t)$ where $p_b(i\Delta t + \Delta t) = u(i\Delta t)$ and $u(i\Delta t)$ is the control action.

10. The method of claim 1, wherein the imaging device comprises a table and a gantry surrounding the table and wherein the table or gantry surrounding the table is adaptively transported to $\hat{p}_b((i+1)\Delta t)$ at time $(i+1)\Delta t$ by setting $u(i\Delta t) = \hat{p}_b(i\Delta t + \Delta t)$.

11. The method of claim 1, wherein the simplified target model is an extended Hammerstein model.

12. The method of claim 11, wherein the extended Hammerstein model is an approximate linear model with some parameters entering nonlinearly.

13. The method of claim 12, wherein predicting the future position of the bolus comprises:
   estimating the parameters $\sigma$, $\tau$ and $t_c$ wherein the movement of the bolus is described by $$b(t, y) = c(t) * \frac{1}{\sigma(y)\sqrt{2\pi}} e^{-\frac{(t-t_c(y))^2}{2\sigma^2(y)}} * \frac{1}{\tau(y)} e^{\frac{t}{\tau(y)}}$$

and wherein the function $c(t)$ is determined by the injection of a bolus into a subject and the parameters $t_c$, $\tau$ and $\sigma$ depend on a location $y$ within the subject.

14. The method of claim 12, wherein the extended Hammerstein model comprises three linear systems $b(t, y_1)$, $b(t, y_2)$, $b(t, y_3)$.

15. The method of claim 14, wherein $y \pm y_1, y_2, y_3, b(t, y)$ is obtained by interpolation.

16. The method of claim 14, wherein $y \pm y_1, y_2, y_3, b(t, y)$ is obtained by extrapolation.

17. The method of claim 12, further comprising inputting an individualized parameter into the extended Hammerstein model.

18. The method of claim 17, wherein the individualized parameter is selected from the group consisting of an ECG signal, heart rate, rhythm, stroke volume, contractility, cardiac preload and cardiac afterload.

19. The method of claim 18, wherein the ECG signal is input into the extended Hammerstein model to predict a surge of the bolus during a systole stage.

20. The method of claim 11, wherein the extended Hammerstein model is described by $$\hat{p}_b(i\Delta t + \Delta t) = \begin{cases} p_b(i\Delta t) & s(k) + q(k) \le i \le s(k+1) \\ p_b(i\Delta t) + c & s(k) = i < s(k) + q(k) \end{cases}$$

for some $q(k)$ and $c$, where $c$ captures the surge of the bolus during the systole stage and $s(k)$ denotes the S phase of a kth ECG signal.

21. The method of claim 20, further comprising inputting an individualized parameter into the extended Hammerstein model.

22. The method of claim 21, wherein the individualized parameter is selected from the group consisting of an ECG signal, heart rate, rhythm, stroke volume, contractility, cardiac preload and cardiac afterload.

23. The method of claim 22, wherein the ECG signal is input into the extended Hammerstein model to predict a surge of the bolus during a systole stage.

24. The method of claim 11, wherein the extended Hammerstein model is a dynamic nonlinear system followed by a linear dynamic system.

25. The method of claim 24, further comprising inputting an individualized parameter into the extended Hammerstein model.

26. The method of claim 25, wherein the individualized parameter is selected from the group consisting of an ECG signal, heart rate, rhythm, stroke volume, contractility, cardiac preload and cardiac afterload.

27. The method of claim 26, wherein the ECG signal is input into the extended Hammerstein model to predict a surge of the bolus during systole.

28. The method of claim 1, wherein the simplified target model is a descriptive model.

29. The method of claim 28, wherein the descriptive model is a fuzzy model.

30. The method of claim 28, wherein the descriptive model is a rule based model.

31. The method of claim 1, wherein the imaging device comprises a table and a gantry surrounding the table and wherein the control action defines the amount, direction and velocity to adaptively transport the table or the gantry surrounding the table to chase the motion of the bolus.

32. The method of claim 1, wherein the control action is determined by a control law.

33. The method of claim 32, wherein the control law is selectable by a user.

34. The method of claim 32, wherein the control law is selected from the group consisting of PID controls, optimal controls, H_inf controls, robust controls, adaptive controls, expert controls, fuzzy controls, and intelligent controls.

35. The method of claim 1, wherein the imaging device comprises a table and a gantry surrounding the table and wherein the table or gantry surrounding the table is adaptively transported by an actuator that moves the table or gantry surrounding the table according to the determined control action.

36. The method of claim 1, wherein the imaging device comprises a table and a gantry surrounding the table and wherein the table and gantry surrounding the table are adaptively transported by an actuator.

37. The method of claim 1, further comprising performing digital subtraction angiography.

38. A system for utilizing bolus propagation and control for contrast enhancement comprising:
an imaging device for measuring a position of a bolus moving along a path in a biological structure;
a predictor comprising a processor programmed for predicting a future position of the bolus using a simplified target model, wherein the simplified target model is a non-parametric model and wherein the predictor predicts the future position of the bolus by estimating the future position by $\hat{p}_b((i+1)\Delta t) = p_b(i\Delta t) + \hat{v}(i\Delta t)\Delta t$, wherein $\hat{v}(i\Delta t)$ and $\hat{p}_b(i\Delta t)$ denote an estimate of the bolus velocity and position $v(i\Delta t)$ and $p_b(i\Delta t)$ at time $i\Delta t$, respectively;
a processor programmed for comparing the predicted future position of the bolus with the measured position of the bolus; and
a controller comprising a processor programmed for determining a control action to eliminate a discrepancy, if any, between the predicted position of the bolus and the measured position of the bolus and an actuator for adaptively adjusting the relative position of the imaging device and the biological structure according to the control action to chase the motion of the bolus.

39. The system of claim 38, wherein the biological structure is positioned on a table and the actuator adaptively adjusts the relative position of the imaging device and the biological structure according to the control action to chase the motion of the bolus by adaptively transporting the table according to the control action.

40. The system of claim 38, wherein the biological structure is positioned on a table and is surrounded by a gantry, and wherein the actuator adaptively adjusts the relative position of the imaging device and the biological structure according to the control action to chase the motion of the bolus by adaptively transporting the gantry according to the control action.

41. The system of claim 38, wherein the biological structure is positioned on a table and is surrounded by a gantry, and wherein the actuator adaptively adjusts the relative position of the imaging device and the biological structure according to the control action to chase the motion of the bolus by adaptively transporting the table and the gantry according to the control action.

42. The system of claim 38, wherein the predictor predicts the future position of the bolus using a simplified target model based on current and past bolus positions and bolus velocities.

43. The system of claim 42, wherein the current and past bolus positions and velocities are provided by imaging reconstruction algorithms.

44. The system of claim 38, further comprising an estimator, wherein the estimator estimates unknown parameters that are input into the simplified target model.

45. The system of claim 38, wherein, $p_b(i\Delta t) = p_b((i-1)\Delta t) + v((i\,i-1)\Delta t)\Delta t.$ 46. The system of claim 38, wherein $\hat{v}(i\Delta t) = \hat{v}((i-1)\Delta t) + \mu[p_b(i\Delta t) - p_b((i-1)\Delta t) - \hat{v}((i-1)\Delta t)\Delta t].$ 47. The system of claim 38, wherein the actuator adaptively transports the imaging device or a portion thereof to $\hat{p}_b((i+1)\Delta t)$ at time $(i+1)\Delta t$ by setting $u(i\Delta t) = \hat{p}_b(i\Delta t + \Delta t)$ where $p_b(i\Delta t + \Delta t)$ and $u(i\Delta t)$ is the control action.

48. The system of claim 38, wherein the imaging device comprises a table and a gantry surrounding the table and the actuator adaptively transports the table or gantry to $\hat{p}_b((i+1)\Delta t)$ at time $(i+1)\Delta t$ by setting $u(i\Delta t) = \hat{p}_b(i\Delta t + \Delta t)$.

49. The system of claim 38, wherein the simplified target model is an extended Hammerstein model.

50. The system of claim 49, wherein the extended Hammerstein model is an approximate linear model with some parameters entering nonlinearly.

51. The system of claim 50, wherein the predictor predicts the future position of the bolus by:
estimating the parameters $\sigma$, $\tau$ and $t_c$ wherein the movement of the bolus is described by $$b(t, y) = c(t) * \frac{1}{\sigma(y)\sqrt{2\pi}} e^{-\frac{(t-t_c(y))^2}{2\sigma^2(y)}} * \frac{1}{\tau(y)} e^{\frac{t}{\tau(y)}}$$

and wherein the function c(t) is determined by the injection of a bolus into a subject and the parameters $t_c$, $\tau$ and $\sigma$ depend on a location y within the subject.

52. The system of claim 50, wherein the extended Hammerstein model comprises three linear systems $b(t, y_1)$, $b(t, y_2)$, $b(t, y_3)$.

53. The system of claim 52, wherein $y \pm y_1, y_2, y_3, b(t, y)$ is obtained by interpolation.

54. The system of claim 52, wherein y±y$_1$, y$_2$, y$_3$, b(t, y) is obtained by extrapolation.

55. The system of claim 49, wherein the predictor predicts the future position of the bolus by:

$$\tilde{p}_b(i\Delta t + \Delta t) = \begin{cases} p_b(i\Delta t) & s(k) + q(k) \leq i \leq s(k+1) \\ p_b(i\Delta t) + c & s(k) = i < s(k) + q(k) \end{cases}$$

for some q(k) and c, where c captures a surge of the bolus during a systole stage and s(k) denotes the S phase of a kth ECG signal.

56. The system of claim 55, further comprising inputting an individualized parameter into the extended Hammerstein model.

57. The system of claim 56, wherein the individualized parameter is selected from the group consisting of an ECG signal, heart rate, rhythm, stroke volume, contractility, cardiac preload and cardiac afterload.

58. The system of claim 57, wherein the ECG signal is input into the extended Hammerstein model to predict a surge of the bolus during systole.

59. The system of claim 38, wherein the simplified target model is a descriptive model.

60. The system of claim 59, wherein the descriptive model is a fuzzy model.

61. The system of claim 59, wherein the descriptive model is a rule based model.

62. The system of claim 38, wherein the imaging device comprises a table and a gantry surrounding the table and wherein the controller determines a control action that defines the amount, direction and velocity for the actuator to adaptively transport the table or the gantry surrounding the table to chase the motion of the bolus.

63. The system of claim 38, wherein the control action is determined by a control law.

64. The system of claim 38, wherein the control law is selectable by a user.

65. The system of claim 64, wherein the control law is selected from the group consisting of PID controls, optimal controls, H_inf controls, robust controls, adaptive controls, expert controls, fuzzy controls, and intelligent controls.

66. The system of claim 38, wherein the imaging device comprises a table and a gantry surrounding the table and wherein the table or gantry surrounding the table is adaptively transported by the actuator which moves the table or gantry surrounding the table according to the determined control action.

67. The system of claim 38, wherein the imaging device comprises a table and a gantry surrounding the table and wherein the table and gantry surrounding the table are adaptively transported by the actuator.

68. A computer readable medium having computer readable program code for utilizing bolus propagation and control for contrast enhancement comprising:
    program code for measuring with an imaging device a position of a bolus moving along a path in a biological structure;
    program code for predicting a future position of the bolus using a simplified target model, wherein the simplified target model is a non-parametric model and wherein predicting the future position of the bolus comprises estimating the future position by $\hat{p}_b((i+1)\Delta t) = p_b(i\Delta t) + \hat{v}(i\Delta t)\Delta t$, wherein $\hat{v}(i\Delta t)$ and $\hat{p}_b(i\Delta t)$ denote an estimate of the bolus velocity and position v(i∆t) and p$_b$(i∆t) at time i∆t, respectively;
    program code for comparing the predicted future position of the bolus with the measured position of the bolus;
    program code for determining a control action to eliminate a discrepancy, if any, between the predicted position of the bolus and the measured position of the bolus; and
    program code for adaptively adjusting the relative position of the imaging device and the biological structure according to the control action to chase the motion of the bolus.

* * * * *